(12) United States Patent
Ben-Ari et al.

(10) Patent No.: US 11,446,323 B2
(45) Date of Patent: Sep. 20, 2022

(54) COMPOSITIONS AND METHODS FOR THE TREATMENT OF FIBROTIC DISEASES

(71) Applicant: Tel HaShomer Medical Research Infrastructure and Services Ltd., Ramat-Gan (IL)

(72) Inventors: Ziv Ben-Ari, Ramat-Gan (IL); Michal Safran, Ramat-Gan (IL); Maya Sultan, Ramat-Gan (IL)

(73) Assignee: Tel HaShomer Medical Research Infrastructure and Services Ltd., Ramat-Gan (IL)

(*) Notice: Subject to any disclaimer, the term of this patent is extended or adjusted under 35 U.S.C. 154(b) by 0 days.

(21) Appl. No.: 16/642,393

(22) PCT Filed: Aug. 30, 2018

(86) PCT No.: PCT/IL2018/050964
§ 371 (c)(1),
(2) Date: Feb. 27, 2020

(87) PCT Pub. No.: WO2019/043709
PCT Pub. Date: Mar. 7, 2019

(65) Prior Publication Data
US 2020/0188424 A1    Jun. 18, 2020

Related U.S. Application Data

(60) Provisional application No. 62/552,477, filed on Aug. 31, 2017.

(51) Int. Cl.
*A61K 31/7105* (2006.01)
*C12N 15/113* (2010.01)
*C12Q 1/68* (2018.01)

(52) U.S. Cl.
CPC ........ *A61K 31/7105* (2013.01); *C12N 15/113* (2013.01); *C12N 2310/141* (2013.01); *C12N 2320/32* (2013.01)

(58) Field of Classification Search
None
See application file for complete search history.

(56) References Cited

U.S. PATENT DOCUMENTS

2017/0290860 A1* 10/2017 Marban ................ C12N 15/113

FOREIGN PATENT DOCUMENTS

| CN | 104524599 | 4/2015 |
|---|---|---|
| JP | 2017-145222 | 8/2017 |
| WO | WO 2014/028493 | 2/2014 |
| WO | WO 2016/054094 | 4/2016 |
| WO | WO 2016/054591 | 4/2016 |
| WO | WO 2017/058938 | 4/2017 |
| WO | WO 2018/231851 | 12/2018 |
| WO | WO 2019/043709 | 3/2019 |
| WO | WO 2019/043709 A9 | 4/2019 |
| WO | WO 2019/043709 A9 | 6/2019 |

OTHER PUBLICATIONS

Shen et al., J. Cell. Mol. Med. vol. 21:986-992, May 2017.*
Supplementary Partial European Search Report and the Provisional Opinion dated May 6, 2021 From the European Patent Office Re. Application No. 18852522.4. (14 Pages).
Bala et al. "Circulating MicroRNAs in Exosomes Indicate Hepatocyte Injury and Inflammation in Alcoholic, Drug-Induced and Inflammatory Liver Diseases", Hepatology, XP055201062, 56(5):1946-1957, Jul. 26, 2012.
Muralidbaran et al. "Extracellular MicroRNA Signature In Chronic Kidney Disease" American Journal of Physiology: Renal Physiology, XP055796018, 312:F982-F991, Jun. 1, 2017.
Oak et al. "A Micro RNA Processing Defectin Rapidly Progressing Idiopathic Pulmonary Fibrosis", PLOS One, XP055031325, 6(6):e21253, Jun. 21, 2011.
Supplementary European Search Report and the European Search Opinion dated Sep. 27, 2021 From the European Patent Office Re. Application No. 18852522.4. (14 Pages).
Song et al. "Loss of MiR-532-5p In Vitro Promotes Cell Proliferation and Metastasis by Influencing CXCL2 Expression in HCC", American Journal of Translational Research, XP055841979, 7(11): 2254-2261, Published Online Nov. 15, 2015.
International Preliminary Report on Patentability dated Mar. 12, 2020 From the International Bureau of WIPO Re. Application No. PCT/IL2018/050964. (10 Pages).
International Search Report and the Written Opinion dated Dec. 30, 2018 From the International Searching Authority Re. Application No. PCT/IL2018/050964. (16 Pages).
Invitation to Pay Additional Fees, Communication Relating to the Results of the Partial International Search dated Nov. 12, 2018 From the International Searching Authority Re. Application No. PCT/IL2018/050964. (5 Pages).
Chen et al. "Hepatocyte Exosomes Attenuate Hepatic Stellate Cell Activation in vitro and are Anti-Fibrotic in vivo", Hepatology, 63(S1): 99A, Abstract 188, Oct. 1, 2016. Abstract.
Hayes et al. "MicroRNAs as Biomarkers for Liver Disease and Hepatocellular Carcinoma", International Journal of Molecular Sciences, 17: 280-1-280-17, Feb. 24, 2016.
Hyun et al. "MicroRNA-378 Limits Activation of Hepatic Stellate Cells and Liver Fibrosis by Suppressing Gli3 Expression", Nature Communications, 7: 10993-1-10993-16, Mar. 22, 2016.
Kitano et al. "Hepatic Stellate Cells and MicroRNAs in Pathogenesis of Liver Fibrosis", Journal of Clinical Medicine, 5(3): 38-1-38-19, Published Online Mar. 16, 2016.
Lee et al. "Exosomes Derived From Palmitic Acid-Treated Hepatocytes Induce Fibrotic Activation of Hepatic Stellate Cells", Scientific Reports, 7: 3710-1-3710-10, Published Online Jun. 16, 2017.
Shen et al. "The Role of Exosomes in Hepatitis, Liver Cirrhosis and Hepatocellular Carcinoma", Journal of Cellular and Molecular Medicine, 21(5): 986-992, Published Online Feb. 22, 2017.

(Continued)

*Primary Examiner* — Sean McGarry

(57) ABSTRACT

A method of treating a disease associated with fibrosis is disclosed. The method comprises administering to the subject a therapeutically effective amount of exosomes isolated from a hepatic cell-conditioned medium. Administration of agents isolated from the exosomes for treatment of fibrotic diseases is also contemplated.

11 Claims, 24 Drawing Sheets

Specification includes a Sequence Listing.

(56) References Cited

OTHER PUBLICATIONS

Tu et al. "MicroRNA-30 Protects Against Carbon Tetrachloride-Induced Liver Fibrosis by Attenuating Transforming Growth Factor Beta Signaling in Hepatic Stellate Cells", Toxicological Sciences, 146(1): 157-169, Advance Access Publication Apr. 24, 2015.

* cited by examiner

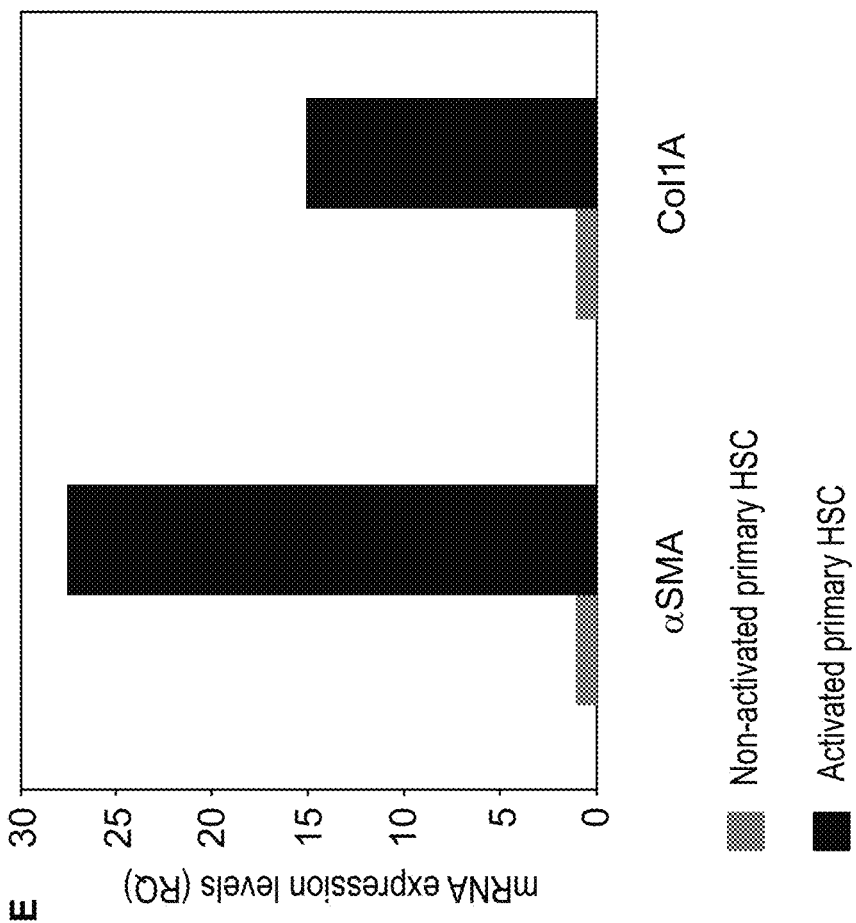
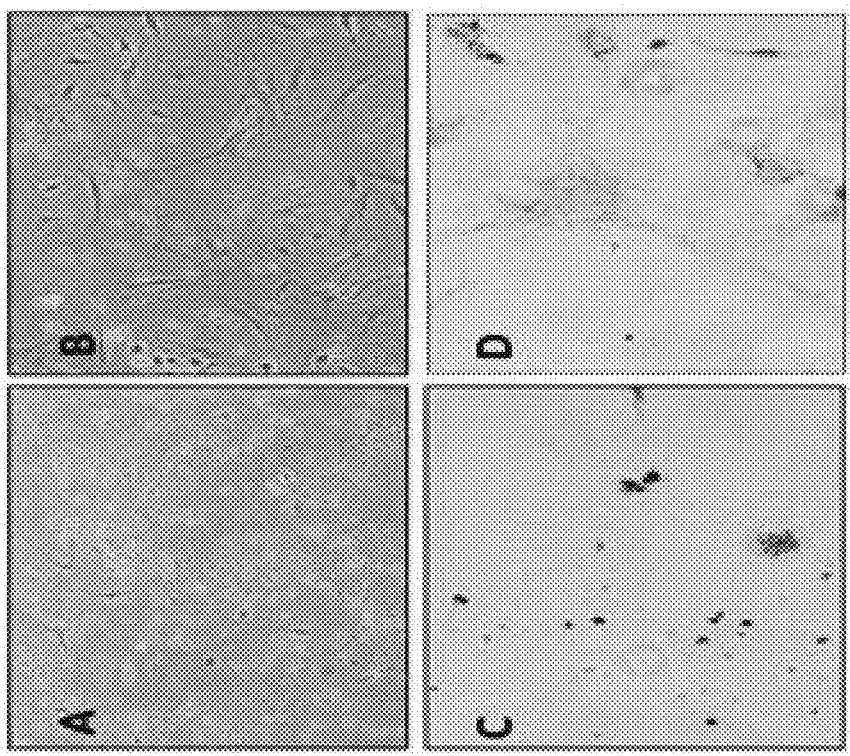

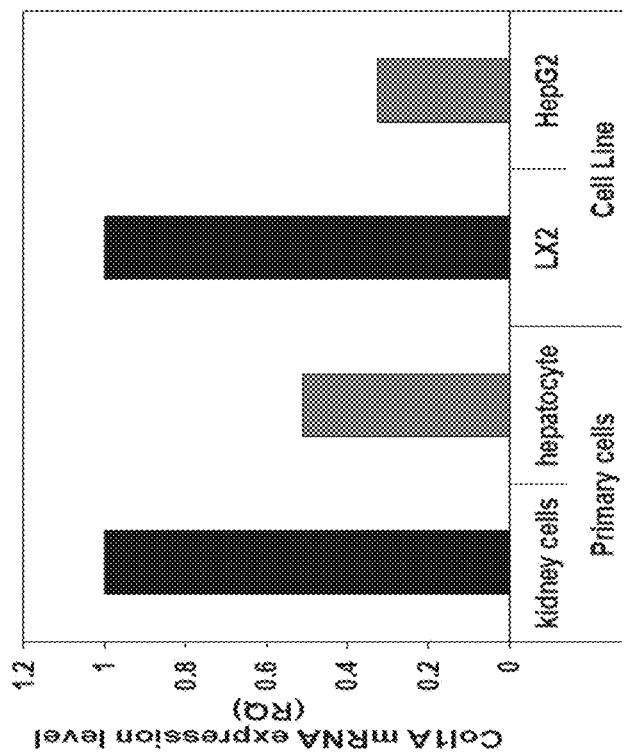
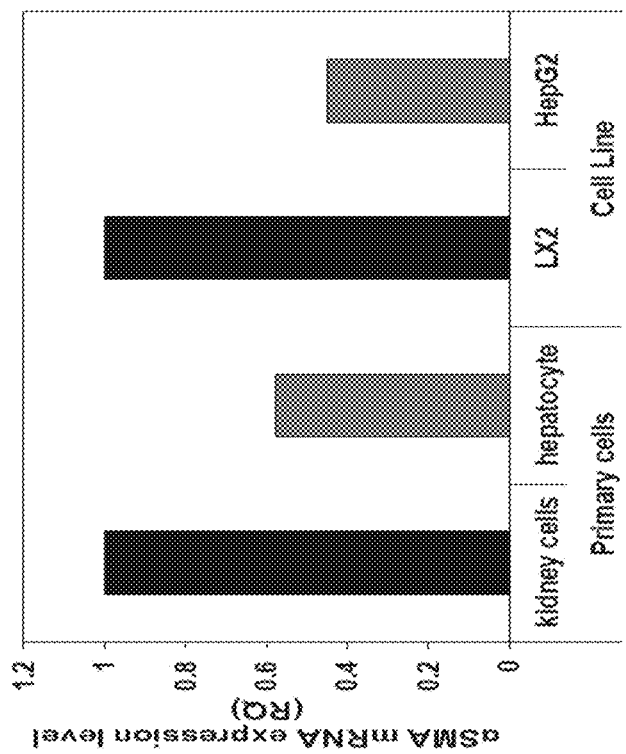
FIG. 6A
FIG. 6B

FIG. 15

| miRNA id | Count(LX2) | Count(Hep) | TPM(LX2) | TPM(Hep) | log2 Ratio | P-value | FDR |
|---|---|---|---|---|---|---|---|
| hsa-miR-452-3p | 0 | 580 | 0.001 | 41.15 | 15.3286 | 8.00E-186 | 9.26E-165 |
| hsa-miR-224-3p | 13 | 12058 | 1 | 855.52 | 9.740658 | 0 | 0 |
| hsa-miR-378 | 4 | 2431 | 0.31 | 172.48 | 9.119945 | 0 | 0 |
| hsa-miR-10b-5p | 287 | 45693 | 21.99 | 3241.95 | 7.20387 | 0 | 0 |
| hsa-miR-99a-3p | 1330 | 126225 | 101.89 | 8955.76 | 6.457731 | 0 | 0 |
| hsa-miR-224-5p | 27 | 1999 | 2.07 | 141.83 | 6.098388 | 0 | 0 |
| hsa-miR-10b-3p | 150 | 10349 | 11.49 | 734.27 | 5.99786 | 0 | 0 |
| hsa-miR-148a-3p | 3332 | 96939 | 255.27 | 6877.89 | 4.75187 | 0 | 0 |
| hsa-let-7a-3p | 3738 | 42065 | 286.38 | 2984.54 | 3.381506 | 0 | 0 |
| hsa-miR-196a-5p | 1832 | 11824 | 140.35 | 838.92 | 2.579504 | 0 | 0 |
| hsa-miR-99b-3p | 2586 | 15830 | 198.12 | 1123.15 | 2.503104 | 0 | 0 |
| hsa-miR-320d | 1435 | 8699 | 109.94 | 617.2 | 2.489022 | 0 | 0 |
| hsa-let-7e-3p | 594 | 3585 | 45.51 | 254.36 | 2.482616 | 0 | 0 |
| hsa-miR-378a-3p | 2707 | 16185 | 207.39 | 1148.34 | 2.469132 | 0 | 0 |
| hsa-miR-183-5p | 355 | 1992 | 27.2 | 141.33 | 2.377389 | 4.40E-249 | 5.70E-248 |
| hsa-miR-532-5p | 1139 | 6238 | 87.26 | 442.59 | 2.342578 | 0 | 0 |
| hsa-miR-30c-2-3p | 266 | 1446 | 20.38 | 102.59 | 2.331664 | 3.22E-177 | 3.83E-176 |
| hsa-miR-3529-3p | 817 | 3932 | 62.59 | 278.98 | 2.156158 | 0 | 0 |
| hsa-miR-3074-5p | 2456 | 11447 | 188.16 | 812.17 | 2.109822 | 0 | 0 |
| hsa-let-7f-1-3p | 2694 | 9742 | 206.39 | 691.2 | 1.74373 | 0 | 0 |
| hsa-let-7c-3p | 4977 | 17933 | 381.3 | 1272.36 | 1.738508 | 0 | 0 |
| hsa-miR-486-5p | 1818 | 6399 | 139.28 | 454.01 | 1.704736 | 0 | 0 |
| hsa-miR-423-5p | 27586 | 127621 | 2113.43 | 9054.8 | 2.099096 | 0 | 0 |

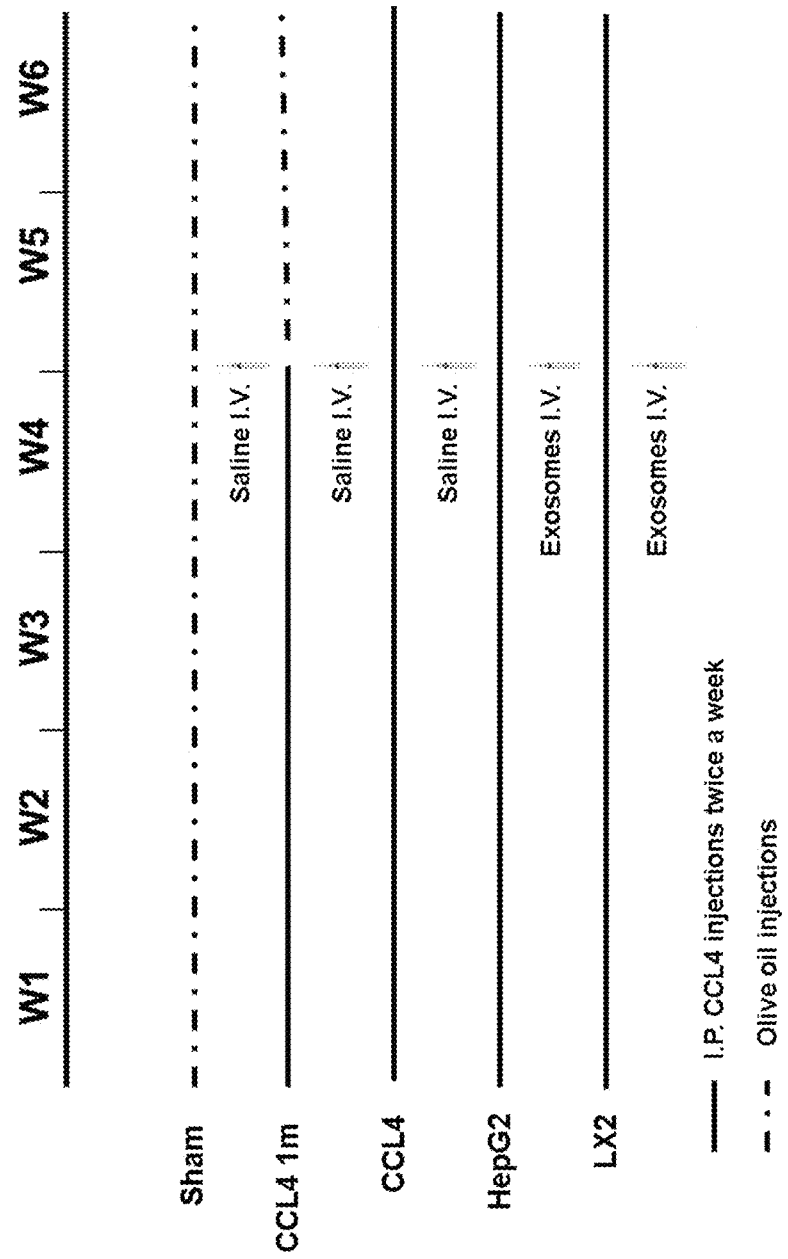

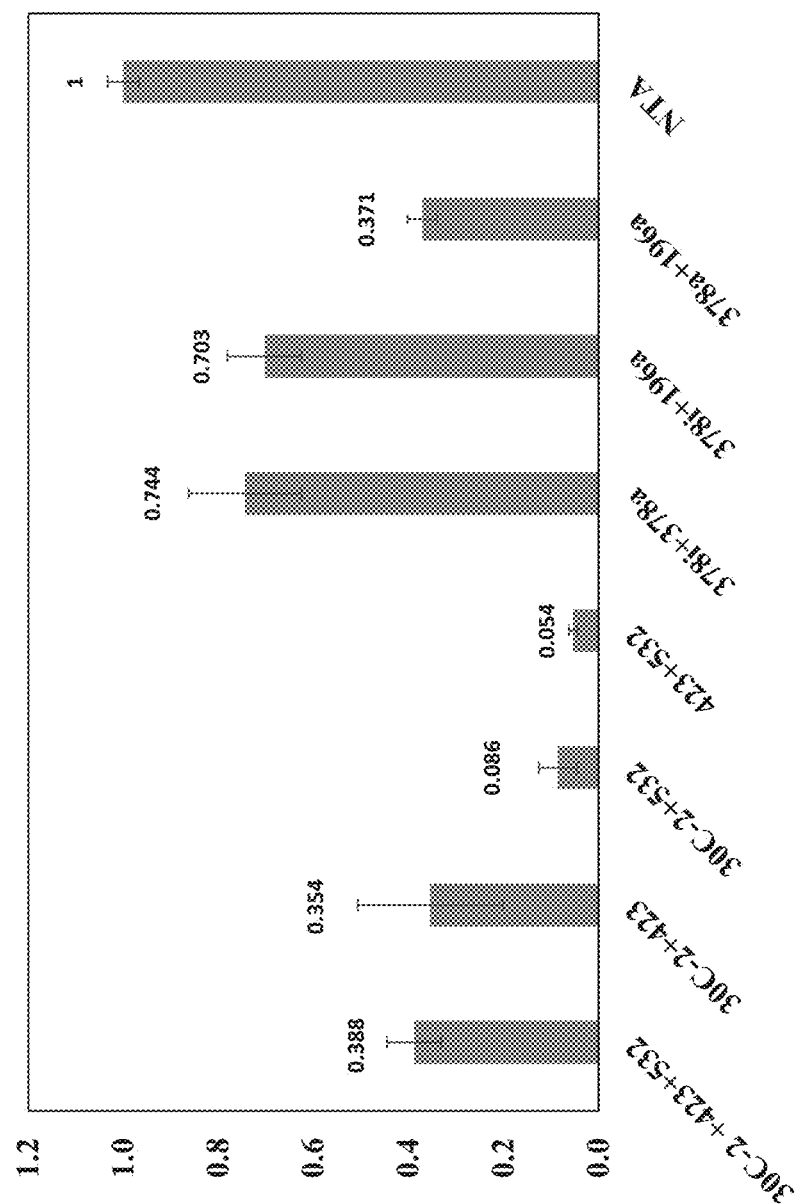

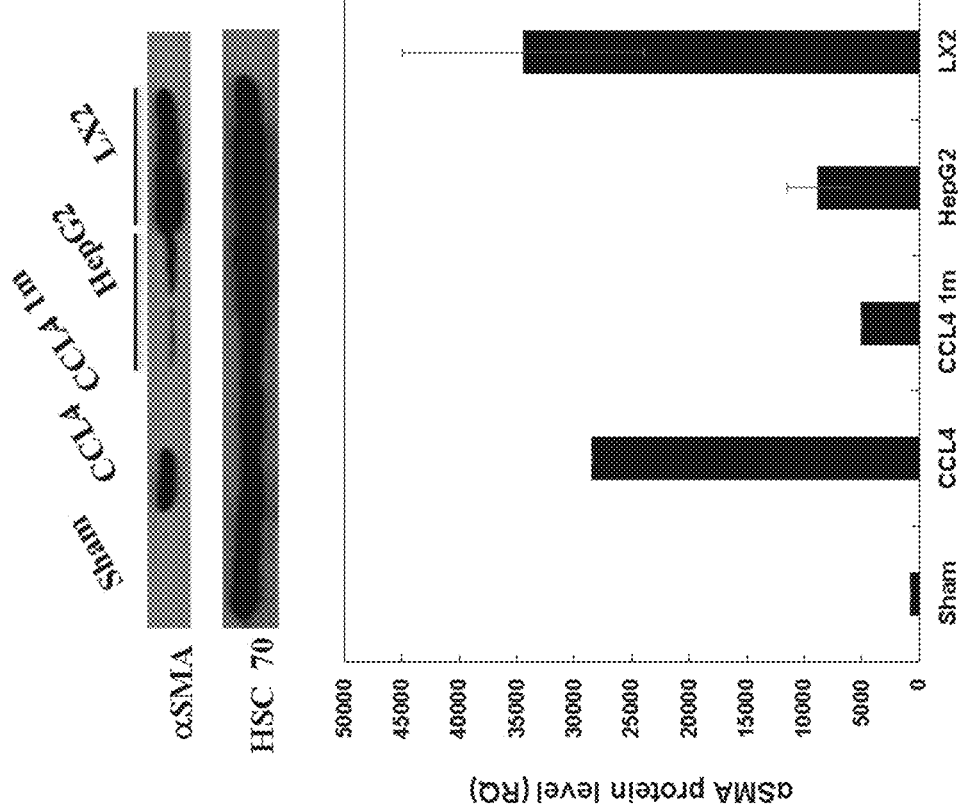

COMPOSITIONS AND METHODS FOR THE TREATMENT OF FIBROTIC DISEASES

SEQUENCE LISTING STATEMENT

The ASCII file, entitled 81245SequenceListing.txt, created on Feb. 27, 2020 comprising 12,510 bytes, submitted concurrently with the filing of this application is incorporated herein by reference. The sequence listing submitted herewith is identical to the sequence listing forming part of the international application.

RELATED APPLICATIONS

This application is a National Phase of PCT Patent Application No. PCT/IL2018/050964 having International filing date of Aug. 30, 2018, which claims the benefit of priority under 35 USC § 119(e) of U.S. Provisional Patent Application No. 62/552,477 filed on Aug. 31, 2017. The contents of the above applications are all incorporated by reference as if fully set forth herein in their entirety.

FIELD AND BACKGROUND OF THE INVENTION

The present invention, in some embodiments thereof, relates to methods for treating fibrosis and, more particularly, but not exclusively, to liver fibrosis.

Fibrosis is the excess accumulation of extracellular matrix (ECM), resulting from chronic, non-resolving inflammation. This inflammation triggers a wound-healing process that mitigates inflammatory tissue destruction but also leads to scar tissue formation. Multiple etiologies underlie development of liver fibrosis, such as chronic viral hepatitis B or C, autoimmune and biliary diseases, alcoholic steatohepatitis (ASH) and, nonalcoholic steatohepatitis (NASH). Fibrosis progression toward cirrhosis, i.e., replacement of functional parenchyma by scar tissue accompanied by severe architectural and vascular distortion, is the major cause of liver-related morbidity and mortality. Patient with cirrhosis are more prone to develop liver failure, portal hypertension or infection and are at higher risk of developing hepatocellular carcinoma (HCC). Liver fibrosis progression rates vary widely among patients and are thus not predictable.

In the normal liver, hepatic stellate cells (HSCs) constitute quiescent, vitamin A—storing cells. Upon activation by specific stimuli released by an injured liver, HSCs undergo "activation" or "transdifferentiation", yielding a myofibroblast-like cell, with several new phenotypic characteristics, such as enhanced cell migration and adhesion, expression of αSMA, increased proliferation and production of chemotactic substances capable of recruiting inflammatory cells as well as other HSCs. Stellate cell activation is a tightly programmed response occurring in a reproducible sequence. The early events, known as "initiation", are associated with transcriptional events and induction of immediate early genes as well as rapid changes in phenotype. These early changes are likely to result from paracrine stimulation by all neighboring cell types, including sinusoidal endothelium, Kupffer cells, hepatocytes, platelets, and leukocytes. "Perpetuation", the second stage of stellate cell activation, involves several discrete changes in cell behavior. During this stage, pro-inflammatory, pro-fibrogenic and pro-mitogenic stimuli are released, and act in an autocrine and paracrine manner, maintaining the activated phenotype. Sustained activation of the cells involves at least seven discrete changes in cell behavior, i.e., proliferation, chemotaxis, fibrogenesis, contractility, matrix degradation, retinoid loss, and white blood cells chemoattractant/cytokine release, consequently leading to increased accumulation of extracellular matrix. Nevertheless, it has been demonstrated that fibrosis and even cirrhosis can be reversible if the underlying cause is successfully eliminated. Understanding the mechanistic pathways and the regulatory factors driving the development of fibrosis and its regression, may give rise to therapeutic approaches as well as novel diagnostic tools for this syndrome.

The ability of the fibrotic liver to revert to a less fibrotic stage or even to normal architecture has been convincingly demonstrated over the last two decades in both rodents and in patients following successful treatment of various underlying hepatic diseases. However not much is known about the mechanism of the "removal/clearance" of activated myofibroblasts from the liver or their inactivation during fibrosis resolution. Recently two studies have demonstrated that although a small number (~2.6%) of activated HSCs are cleared during fibrosis resolution via apoptosis, most of them undergo a reversal mechanism back to their quiescent state [Troeger, J. S., et al., Gastroenterology, 2012. 143(4): p. 1073-83 e22; Kisseleva, T., et al., Proc Natl Acad Sci USA, 2012. 109(24): p. 9448-53].

Although there is a similarity between these inactivated HSCs, they are not identical to the quiescent non-activated cells, thus, they are more susceptible to a second round of fibrogenesis stimulation.

Background art includes Kitano and Bloomston, J Clin Med, 2016 March; 5(3):38; Hayes and Chayama, Int. J. Mol. Sci. 2016, 17, 280; doi:10.3390; Lee et al., Scientific Reports|7: 3710|DOI:10.1038/s41598-017-03389-2; Hyun et al., Nature Communications 7:10993|DOI: 10.1038/ncomms10993, Szabo and Bala., Nat Rev Gastroenterol Hepatol. 2013 September; 10(9): 542-552; and Shen et al., J Cell Mol Med. 2017 May; 21(5): 986-992.

SUMMARY OF THE INVENTION

According to an aspect of some embodiments of the present invention there is provided a method of treating a disease associated with fibrosis in a subject in need thereof comprising administering to the subject a therapeutically effective amount of at least one miRNA selected from the group consisting of hsa-miR-452-3p, hsa-miR-224-3p, hsa-miR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-196b-5p, hsa-miR-148a-3p, hsa-miR-452-5p, hsa-miR-873-5p, hsa-miR-873-3p, hsa-let-7a-3p, hsa-miR-208b-3p, hsa-miR-582-3p, hsa-miR-196a-5p, hsa-miR-99b-3p, hsa-miR-320d, hsa-let-7e-3p, hsa-miR-183-5p, hsa-miR-532-5p, hsa-miR-30c-2-3p, novel_mir18, hsa-miR-3529-3p, hsa-miR-3074-5p, hsa-miR-423-5p, hsa-let-7f-1-3p, hsa-let-7c-3p, hsa-miR-378c, hsa-miR-486-5p, hsa-miR-185-3p, hsa-miR-320e, hsa-miR-182-5p, novel_mir78, hsa-miR-340-3p, hsa-miR-24-2-5p, hsa-miR-330-3p, hsa-miR-192-3p, hsa-miR-26a-2-3p, hsa-miR-26b-3p, hsa-miR-99a-5p, hsa-miR-148b-3p, hsa-miR-374a-3p, hsa-miR-30a-3p, novel-mir32, hsa-miR-17-3p, hsa-miR-193b-5p, hsa-let-7i-5p and hsa-miR-19b-3p, thereby treating the disease associated with fibrosis.

According to an aspect of some embodiments of the present invention there is provided a method of treating a disease associated with fibrosis in a subject in need thereof comprising administering to the subject a therapeutically effective amount of at least two miRNAs selected from the group consisting of hsa-miR-452-3p, hsa-miR-224-3p, hsamiR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-196b-5p, hsa-miR-148a-3p, hsa-miR-452-5p, hsa-miR-873-5p, hsa-miR-873-3p, hsa-let-7a-3p, hsa-miR-208b-3p, hsa-miR-582-3p, hsa-miR-196a-5p, hsa-miR-99b-3p, hsa-miR-320d, hsa-let-7e-3p, hsa-miR-378a-3p, hsa-miR-183-5p, hsa-miR-532-5p, hsa-miR-30c-2-3p, novel_mir18, hsa-miR-3529-3p, hsa-miR-3074-5p, hsa-miR-423-5p, hsa-let-7f-1-3p, hsa-let-7c-3p, hsa-miR-378c, hsa-miR-486-5p, hsa-miR-185-3p, hsa-miR-320e, hsa-miR-182-5p, novel_mir78, hsa-miR-340-3p, hsa-miR-24-2-5p, hsa-miR-330-3p, hsa-miR-192-3p, hsa-miR-26a-2-3p, hsa-miR-26b-3p, hsa-miR-99a-5p, hsa-miR-148b-3p, hsa-miR-374a-3p, hsa-miR-30a-3p, novel-mir32, hsa-miR-17-3p, hsa-miR-193b-5p, hsa-let-7i-5p and hsa-miR-19b-3p, thereby treating the disease associated with fibrosis.

According to an aspect of some embodiments of the present invention there is provided a method of treating hepatic fibrosis in a subject in need thereof comprising administering to the subject a therapeutically effective amount of at least one miRNA selected from the group consisting of miRNA-30c-2-3p, miRNA-423-5p and miRNA-532-5p.

According to an aspect of some embodiments of the present invention there is provided a method of treating a disease associated with fibrosis in a subject in need thereof comprising administering to the subject a therapeutically effective amount of exosomes isolated from a hepatic cell-conditioned medium, thereby treating the disease associated with fibrosis.

According to an aspect of some embodiments of the present invention there is provided a method of selecting an agent useful for treating a disease associated with fibrosis comprising:

(a) contacting the agent with primary hepatic stellate cells; and (b) analyzing whether the primary hepatic stellate cells differentiate towards myofibroblasts, wherein if the agent prevents differentiation of the primary hepatic stellate cells towards the myofibroblasts, it is indicative that the agent is useful for treating the disease associated with fibrosis.

According to some embodiments of the invention, the miRNA is selected from the group consisting of hsa-miR-452-3p, hsa-miR-224-3p, hsa-miR-378i, hsa-miR-10b-5p, hsa-miR-99a-3p, hsa-miR-224-5p, hsa-miR-10b-3p, hsa-miR-148a-3p, has-let-7a-3p, hsa-miR-196a-5p, hsa-miR-99b-3p, hsa-miR-320d, hsa-let-7e-3p, hsa-miR-1835p, hsa-miR-532-5p, hsa-miR-30c-2-3p, hsa-miR-3529-3p, hsa-miR-3074-5p, hsa-let-7f-1-3p, hsa-let-7c-3p, hsa-miR-486-5p and hsa-miR-423-5p.

According to some embodiments of the invention, the miRNA is selected from the group consisting of miR-196a-5p and miR-378i.

According to some embodiments of the invention, the at least one miRNA is comprised in a particle.

According to some embodiments of the invention, the at least one miRNA comprises miRNA-423-5p and miRNA-532-5p.

According to some embodiments of the invention, the at least one miRNA comprises miRNA-30c-2-3p and miRNA-532-5p.

According to some embodiments of the invention, the particle is a liposome.

According to some embodiments of the invention, the particle is an exosome.

According to some embodiments of the invention, the exosome is secreted from hepatic cells.

According to some embodiments of the invention, the hepatic cells are non-diseased hepatic cells.

According to some embodiments of the invention, the exosome is an isolated exosome.

According to some embodiments of the invention, the miRNA is selected from the group consisting of hsa-miR-452-3p, hsa-miR-224-3p, hsa-miR-378i, hsa-miR-10b-5p, hsa-miR-99a-3p, hsa-miR-224-5p, hsa-miR-10b-3p, hsa-miR-148a-3p, has-let-7a-3p, hsa-miR-196a-5p, hsa-miR-99b-3p, hsa-miR-320d, hsa-let-7e-3p, hsa-miR-378a-3p, hsa-miR-1835p, hsa-miR-532-5p, hsa-miR-30c-2-3p, hsa-miR-3529-3p, hsa-miR-3074-5p, hsa-let-7f-1-3p, hsa-let-7c-3p, hsa-miR-486-5p and hsa-miR-423-5p.

According to some embodiments of the invention, the miRNA is selected from the group consisting of miR-196a-5p, miR378a-3p and miR-378i.

According to some embodiments of the invention, the hepatic cells comprise primary hepatic cells.

According to some embodiments of the invention, the hepatic cells comprise transformed hepatic cells.

According to some embodiments of the invention, the at least one miRNA is comprised in a hepatic cell-conditioned medium.

According to some embodiments of the invention, the at least one miRNA is an isolated miRNA.

According to some embodiments of the invention, the disease is a hepatic disease.

According to some embodiments of the invention, the hepatic disease is selected from the group consisting of hepatitis, an autoimmune hepatic disease, alcoholic steatohepatitis (ASH) and non-alcoholic steatohepatitis (NASH).

According to some embodiments of the invention, the hepatitis is chronic viral hepatitis B or chronic viral hepatitis A.

According to some embodiments of the invention, the analyzing is effected by analyzing the expression of at least one of αSMA and/or Col1A.

According to some embodiments of the invention, the analyzing is effected by analyzing the expression of at least one marker selected from the group consisting of PDGF, TGFβ, TIMP1, TIMP2, αSMA and Col1A.

According to some embodiments of the invention, the analyzing is effected by visualizing the cells using a stain.

According to some embodiments of the invention, the agent is comprised in an exosome secreted from hepatic cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E illustrate phenotypic and transcriptional alterations in HSCs after activation/differentiation to myoblast-like cells. HSCs were isolated from mouse liver by enzymatic digestion. The cells were separated from parenchymal and non-parenchymal cells on a 10% idoxinol gradient and plated in 10% FCS DMEM medium. Cell were harvested on the same day (A,C) or 96 hours after isolation (B,D). Inverted microscopy was used to visualize the cells (A,B). Oil Red O staining of non-activated (C) and activated (D) cells, was performed using a standard protocol. RNA was purified from the activated and non-activated cells and the levels of αSMA and Col1A transcripts were measured using qRT-PCR (E).

FIGS. 6A-B: Hepatocyte-conditioned medium inhibits the activation of differentiated HSCs. Primary HSCs were purified from mouse liver and grown in culture for 7 days. The culture medium was then changed to medium collected from primary hepatocytes, primary kidney cells, hepatoma cell line or HSC cell line. After an additional 7 days in culture, αSMA and Col1A expression level in the HSCs was evaluated using qRT-PCR.

FIG. 15: List of miRNA present in the HepG2 but not in the LX2 secreted exosomes.

FIG. 18 illustrates the scheme of the fibrosis in-vivo model protocol.

FIG. 19 illustrates that combinations of miRNA mimics detected in HepG2 exosomes can inhibit primary HSC activation. Primary HSCs were transfected with different combinations of the miRNA mimics. Cells were harvested and the levels of αSMA and Col1A expression were measured by RT-qPCR.

FIGS. 20A-E illustrates that hepatocyte exosomes can inhibit the development of fibrosis in-vivo. Hepatic fibrosis was induced in C57BL6 mice as described in FIG. 18. Briefly, mice were injected with CCL4 (1 ml/Kg) for 6 weeks, after the $4^{th}$ week the mice were treated with exosomes secreted either from LX2 or HepG2 or PBS as a control. After an additional 2 weeks, the mice were sacrificed, serum and liver samples were collected. Liver enzyme levels were detected (A) RNA and protein were purified and the levels of hepatic fibrosis markers (αSMA, Col1A, PDGF, TGFβ, TIMP1 and TIMP2) were detected using RT-PCR (B) and Western blot analysis (C). Liver samples were immunohistostained using either H&E (D) or Masson's trichrome reagent (E).

DESCRIPTION OF SPECIFIC EMBODIMENTS OF THE INVENTION

The present invention, in some embodiments thereof, relates to methods for treating fibrosis and, more particularly, but not exclusively, to liver fibrosis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Hepatic fibrosis ensues secondary to chronic hepatic injury and inflammation and some of the common etiologies are viral and autoimmune hepatitis, alcohol consumption, non-alcoholic steatohepatitis (NASH), metabolic diseases leading to copper or iron overload, toxins, and biliary obstruction. It is characterized and accompanied by deposition of extracellular matrix (ECM) with distortion of normal hepatic parenchyma, eventually leading to dense fibrosis, cirrhosis, and development of portal hypertension.

Hepatic stellate cells (HSCs) are liver-specific mesenchymal cells located in the perisinusoidal space known as the space of Disse. Their quiescent form comprises about 5%-8% of all cells in the liver. They play a central role in hepatic development, regeneration, lipoprotein and retinoid metabolism, immune regulation in normal livers, and fibrogenesis in response to hepatic injury. In response to injury, they become activated and lose their normal role of retinoid storage. They proliferate and secrete ECM proteins such as collagen, glycoprotein, and proteoglycans leading to hepatic fibrosis.

Generation of a primary hepatic stellate cell culture allows for the investigation of the molecular mechanisms leading to hepatic fibrosis in a well-controlled manner and to the identification and characterization of different factors which play a role in the process of fibrosis.

Using such primary cell cultures, the present inventors have found that conditioned medium from hepatocytes can inhibit and even reverse the activation of HSCs (FIGS. 2A-B and 3A-C). By purifying and characterizing the factor/factors in the conditioned medium, the present inventors have identified hepatocyte-secreted exosomes as playing a major role in maintaining HSCs in a quiescent state (FIGS. 8-13).

Figure 14:
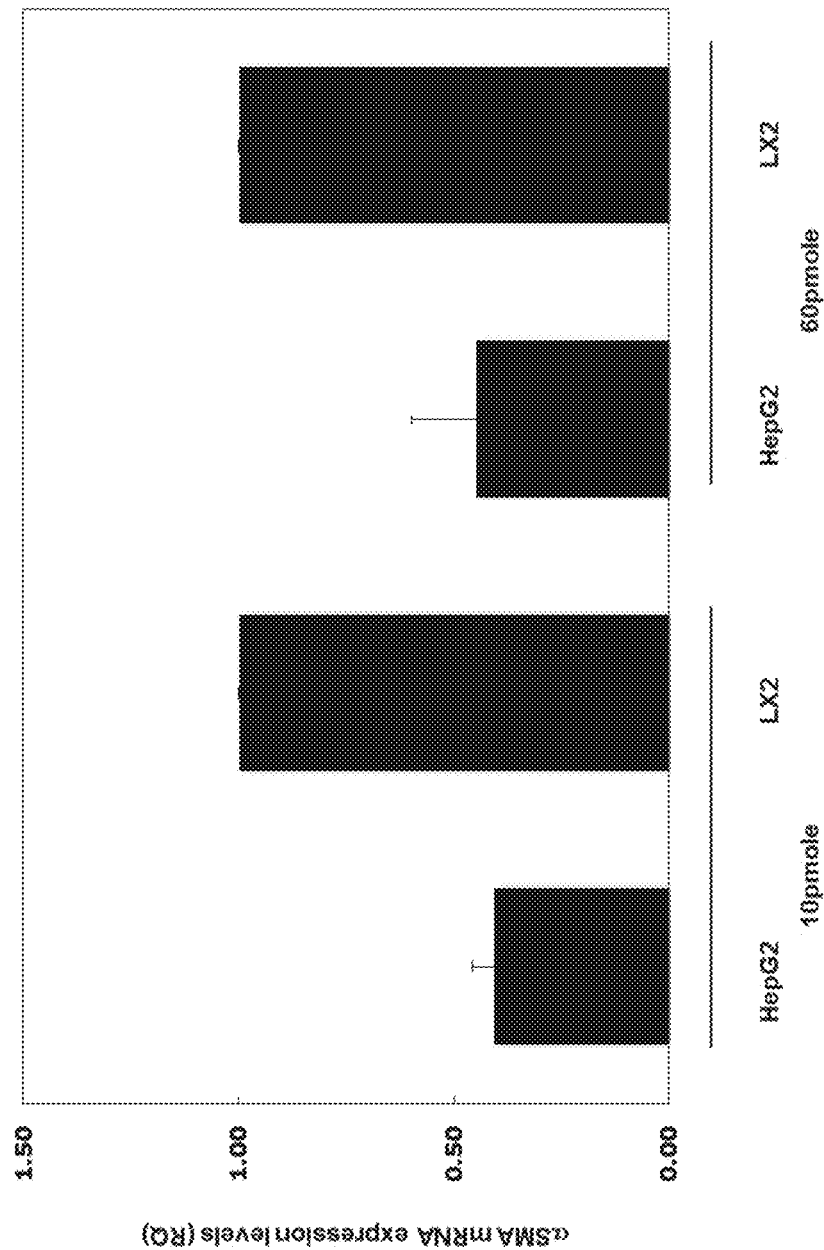
FIG. 14: RNA molecules purified from HepG2 exosomes can inhibit primary HSC activation. RNA was extracted from purified HepG2 and LX2 secreted exosomes. Primary HSCs were transfected with different concentrations of the RNA molecules. 48 hours later the cells were harvested and the levels of αSMA and Col1A expression were measured using RT-qPCR.
Figure 16:
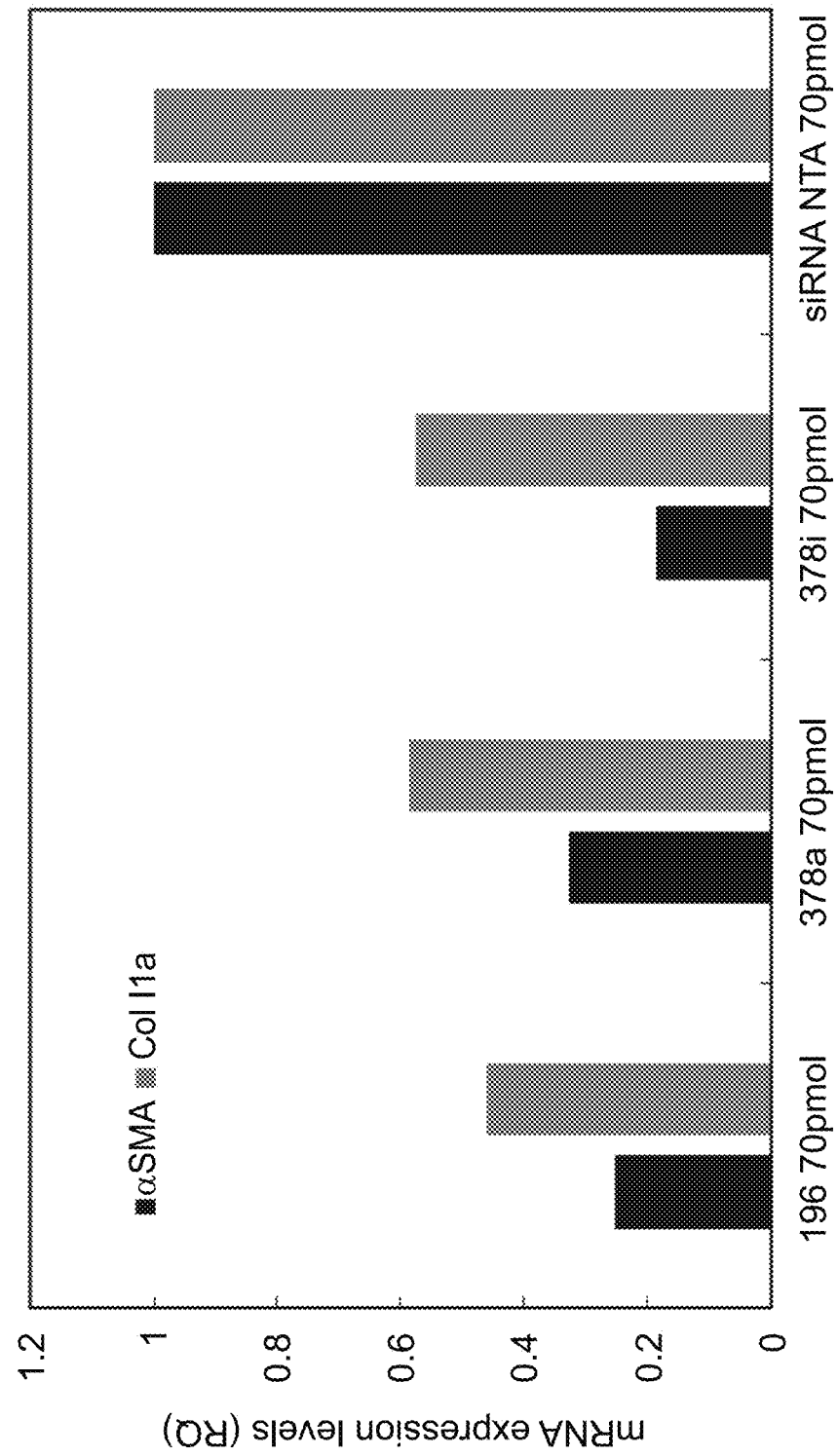
FIG. 16: miRNA mimics found in HepG2 exosomes can inhibit primary HSCs activation. Primary HSCs were transfected with 70 pmol of the miRNA mimics described. 48 hours later the cells were harvested and the levels of αSMA and Col1A expression were measured using RT-qPCR.

Whilst further reducing the present invention to practice, the present inventors identified RNA molecules as being the active component in the exosomes (FIG. 14). They compared miRNAs which were selectively secreted from liver cell derived exosomes to miRNAs that were selectively secreted from kidney cell-derived exosomes and constructed a list of potential miRNAs that may be involved in HSC maintenance (FIG. 15). Three of these miRNAs were validated (FIG. 16).

Consequently, the present teachings suggest that agents which are found specifically in exosomes derived from liver cells (and not exosomes from other cell types) may be useful for treating fibrosis in general and liver fibrosis in particular.

Thus, according to a first aspect of the present invention, there is provided a method of preventing primary hepatic stellate cell differentiation towards a myofibroblast comprising contacting the cells with at least one miRNA selected from the group consisting of hsa-miR-452-3p, hsa-miR-516a-3p, hsa-miR-4664-3p, novel_mir10, hsa-miR-3687, novel_mir74, hsa-miR-522-3p, hsa-miR-6720-3p, hsa-miR-3910, hsa-miR-767-3p, novel_mir17, hsa-miR-675-3p, novel_mir56, hsa-miR-6130, novel_mir93, hsa-miR-516a-5p, hsa-miR-224-3p, hsa-miR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-105-5p, hsa-miR-196b-5p, hsa-miR-196b-5p, hsa-miR-148a-3p, hsa-miR-452-5p, novel_mir45, hsa-miR-873-5p, hsa-miR-148a-5p, hsa-miR-577, hsa-miR-1247-3p, hsa-miR-3936, hsa-miR-4746-3p, hsa-miR-6866-3p, hsa-miR-873-3p, hsa-let-7a-3p, hsa-miR-4792, hsa-miR-3665, hsa-miR-208b-3p, hsa-miR-3065-3p, novel_mir86, hsa-miR-664b-5p, hsa-miR-378d, novel_mir44, hsa-miR-378f, hsa-miR-365b-3p, hsa-miR-582-3p, hsa-miR-499b-3p, hsa-miR-6805-5p, hsa-miR-196a-5p, hsa-miR-99b-3p, hsa-miR-320d, hsa-let-7e-3p, hsa-miR-378a-3p, hsa-miR-183-5p, hsa-miR-532-5p, hsa-miR-30c-2-3p, novel_mir18, hsa-miR-3529-3p, hsa-miR-3074-5p, hsa-miR-423-5p, hsa-miR-32-5p, hsa-miR-330-5p, hsa-miR-215-5p, hsa-miR-96-3p, hsa-miR-34a-3p, hsa-let-7f-1-3p, hsa-let-7c-3p, hsa-miR-378c, hsa-miR-486-5p, hsa-miR-185-3p, hsa-miR-320e, hsa-miR-182-5p, novel_mir54, novel_mir78, hsa-miR-340-3p, hsa-miR-129-1-3p, hsa-miR-365a-5p, hsa-miR-140-5p, hsa-miR-24-2-5p, hsa-miR-330-3p, hsa-miR-192-3p, hsa-miR-26a-2-3p, hsa-miR-219a-1-3p, hsa-miR-26b-3p, hsa-miR-99a-5p, hsa-miR-148b-3p, hsa-miR-584-3p, hsa-miR-374a-3p, novel_mir80, hsa-miR-30a-3p, novel_mir32, novel_mir55, hsa-miR-4448, hsa-miR-17-3p, hsa-miR-193b-5p, hsa-let-7i-5p and hsa-miR-19b-3p.

In one embodiment, the miRNA is selected from the group consisting of hsa-miR-452-3p, hsa-miR-224-3p, hsa-miR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-196b-5p, hsa-miR-148a-3p, hsa-miR-452-5p, hsa-miR-873-5p, hsa-miR-873-3p, hsa-let-7a-3p, hsa-miR-208b-3p, hsa-miR-582-3p, hsa-miR-196a-5p, hsa-miR-99b-3p, hsa-miR-320d, hsa-let-7e-3p, hsa-miR-378a-3p, hsa-miR-183-5p, hsa-miR-532-5p, hsa-miR-30c-2-3p, novel_mir18, hsa-miR-3529-3p, hsa-miR-3074-5p, hsa-miR-423-5p, hsa-let-7f-1-3p, hsa-let-7c-3p, hsa-miR-378c, hsa-miR-486-5p, hsa-miR-185-3p, hsa-miR-320e, hsa-miR-182-5p, novel_mir78, hsa-miR-340-3p, hsa-miR-24-2-5p, hsa-miR-330-3p, hsa-miR-192-3p, hsa-miR-26a-2-3p, hsa-miR-26b-3p, hsa-miR-99a-5p, hsa-miR-148b-3p, hsa-miR-374a-3p, hsa-miR-30a-3p, novel-mir32, hsa-miR-17-3p, hsa-miR-193b-5p, hsa-let-7i-5p and hsa-miR-19b-3p.

In still another embodiment, the miRNA is selected from the group consisting of hsa-miR-452-3p, hsa-miR-224-3p, hsa-miR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-196b-5p, hsa-miR-148a-3p, hsa-miR-452-5p, hsa-miR-873-5p, hsa-miR-873-3p, hsa-let-7a-3p, hsa-miR-208b-3p, hsa-miR-582-3p, hsa-miR-196a-5p, hsa-miR-99b-3p, hsa-miR-320d, hsa-let-7e-3p, hsa-miR-183-5p, hsa-miR-532-5p, hsa-miR-30c-2-3p, novel_mir18, hsa-miR-3529-3p, hsa-miR-3074-5p, hsa-miR-423-5p, hsa-let-7f-1-3p, hsa-let-7c-3p, hsa-miR-378c, hsa-miR-486-5p, hsa-miR-185-3p, hsa-miR-320e, hsa-miR-182-5p, novel_mir78, hsa-miR-340-3p, hsa-miR-24-2-5p, hsa-miR-330-3p, hsa-miR-192-3p, hsa-miR-26a-2-3p, hsa-miR-26b-3p, hsa-miR-99a-5p, hsa-miR-148b-3p, hsa-miR-374a-3p, hsa-miR-30a-3p, novel-mir32, hsa-miR-17-3p, hsa-miR-193b-5p, hsa-let-7i-5p and hsa-miR-19b-3p.

In still another embodiment, the miRNA is selected from the group consisting of hsa-miR-452-3p, hsa-miR-224-3p, hsa-miR-378i, hsa-miR-10b-5p, hsa-miR-99a-3p, hsa-miR-224-5p, hsa-miR-10b-3p, hsa-miR-148a-3p, has-let-7a-3p, hsa-miR-196a-5p, hsa-miR-99b-3p, hsa-miR-320d, hsa-let-7e-3p, hsa-miR-378a-3p, hsa-miR-1835p, hsa-miR-532-5p, hsa-miR-30c-2-3p, hsa-miR-3529-3p, hsa-miR-3074-5p, hsa-let-7f-1-3p, hsa-let-7c-3p, hsa-miR-486-5p and hsa-miR-423-5p.

In still another embodiment, the miRNA is selected from the group consisting of miR-196a-5p, miR378a-3p, miR-30c-2-3p, miR-423-5p, miR-532-5p and miR-378i.

In one embodiment, the miRNA is miR-196a-5p and/or miR-378i.

In another embodiment, the miRNA is miR-30c-2-3p, miR-423-5p and/or miR-532-5p.

In still a further embodiment, the miRNA is a combination of both miRNA-423-5p and miRNA-532-5p or a combination of both miRNA-30c-2-3p and miRNA-532-5p.

The sequences of exemplary miRNAs are provided in Table 1 herein below:

TABLE 1

| | | |
|---|---|---|
| hsa-miR-452-3p | CUCAUCUGCAAAGAAGUAAGUG | SEQ ID NO: 7 |
| hsa-miR-224-3p | AAAAUGGUGCCCUAGUGACUACA | SEQ ID NO: 8 |
| hsa-miR-378i | ACUGGACUAGGAGUCAGAAGG | SEQ ID NO: 9 |
| hsa-miR-10b-5p | UACCCUGUAGAACCGAAUUUGUG | SEQ ID NO: 10 |
| hsa-miR-99a-3p | CAAGCUCGCUUCUAUGGGUCUG | SEQ ID NO: 11 |
| hsa-miR-105-3p | ACGGAUGUUUGAGCAUGUGCUA | SEQ ID NO: 12 |
| hsa-miR-224-5p | CAAGUCACUAGUGGUUCCGUU | SEQ ID NO: 13 |
| hsa-miR-10b-3p | ACAGAUUCGAUUCUAGGGGAAU | SEQ ID NO: 14 |
| hsa-miR-338-5p | AACAAUAUCCUGGUGCUGAGUG | SEQ ID NO: 15 |
| hsa-miR-767-5p | UGCACCAUGGUUGUCUGAGCAUG | SEQ ID NO: 16 |
| hsa-miR-196b-5p | UAGGUAGUUUCCUGUUGUUGGG | SEQ ID NO: 17 |
| hsa-miR-148a-3p | UCAGUGCACUACAGAACUUUGU | SEQ ID NO: 18 |
| hsa-miR-452-5p | AACUGUUUGCAGAGGAAACUGA | SEQ ID NO: 19 |
| hsa-miR-873-5p | GCAGGAACUUGUGAGUCUCCU | SEQ ID NO: 20 |
| hsa-miR-873-3p | GGAGACUGAUGAGUUCCCGGGA | SEQ ID NO: 21 |
| hsa-let-7a-3p | CUAUACAAUCUACUGUCUUUC | SEQ ID NO: 22 |
| hsa-miR-208b-3p | AUAAGACGAACAAAAGGUUUGU | SEQ ID NO: 23 |
| hsa-miR-582-3p | UAACUGGUUGAACAACUGAACC | SEQ ID NO: 24 |
| hsa-miR-196a-5p | UAGGUAGUUUCAUGUUGUUGGG | SEQ ID NO: 25 |
| hsa-miR-99b-3p | CAAGCUCGUGUCUGUGGGUCCG | SEQ ID NO: 26 |
| hsa-miR-320d | AAAAGCUGGGUUGAGAGGA | SEQ ID NO: 27 |
| hsa-let-7e-3p | CUAUACGGCCUCCUAGCUUUCC | SEQ ID NO: 28 |
| hsa-miR-378a-3p | ACUGGACUUGGAGUCAGAAGGC | SEQ ID NO: 29 |

TABLE 1-continued

| | | |
|---|---|---|
| hsa-miR-183-5p | UAUGGCACUGGUAGAAUUCACU | SEQ ID NO: 31 |
| hsa-miR-532-5p | CAUGCCUUGAGUGUAGGACCGU | SEQ ID NO: 31 |
| hsa-miR-30c-2-3p | CUGGGAGAAGGCUGUUUACUCU | SEQ ID NO: 32 |
| novel_mir18 | GCCUGUCUGAGCGUCGCU | SEQ ID NO: 33 |
| hsa-miR-3529-3p | AACAACAAAAUCACUAGUCUUCCA | SEQ ID NO: 34 |
| hsa-miR-3074-5p | GUUCCUGCUGAACUGAGCCAG | SEQ ID NO: 35 |
| hsa-miR-423-5p | UGAGGGGCAGAGAGCGAGACUUU | SEQ ID NO: 36 |
| hsa-let-7f-1-3p | CUAUACAAUCUAUUGCCUUCCC | SEQ ID NO: 37 |
| hsa-let-7c-3p | CUGUACAACCUUCUAGCUUUCC | SEQ ID NO: 38 |
| hsa-miR-378c | ACUGGACUUGGAGUCAGAAGAGUGG | SEQ ID NO: 39 |
| hsa-miR-486-5p | UCCUGUACUGAGCUGCCCCGAG | SEQ ID NO: 40 |
| hsa-miR-185-3p | AGGGGCUGGCUUUCCUCUGGUC | SEQ ID NO: 41 |
| hsa-miR-320e | AAAGCUGGGUUGAGAAGG | SEQ ID NO: 42 |
| hsa-miR-182-5p | UUUGGCAAUGGUAGAACUCACACU | SEQ ID NO: 43 |
| novel_mir78 | GGAGAAGCCGGCGGGAGC | SEQ ID NO: 44 |
| hsa-miR-340-3p | UCCGUCUCAGUUACUUUAUAGC | SEQ ID NO: 45 |
| hsa-miR-24-2-5p | UGCCUACUGAGCUGAAACACAG | SEQ ID NO: 46 |
| hsa-miR-330-3p | GCAAAGCACACGGCCUGCAGAGA | SEQ ID NO: 47 |
| hsa-miR-192-3p | CUGCCAAUUCCAUAGGUCACAG | SEQ ID NO: 48 |
| hsa-miR-26a-2-3p | CCUAUUCUUGAUUACUUGUUUC | SEQ ID NO: 49 |
| hsa-miR-26b-3p | CCUGUUCUCCAUUACUUGGCUC | SEQ ID NO: 50 |
| hsa-miR-99a-5p | AACCCGUAGAUCCGAUCUUGUG | SEQ ID NO: 51 |
| hsa-miR-148b-3p | UCAGUGCAUCACAGAACUUUGU | SEQ ID NO: 52 |
| hsa-miR-374a-3p | CUUAUCAGAUUGUAUUGUAAUU | SEQ ID NO: 53 |
| hsa-miR-30a-3p | CUUUCAGUCGGAUGUUUGCAGC | SEQ ID NO: 54 |
| novel_mir32 | UUCGUGGGGAACCUGGCGCU | SEQ ID NO: 55 |

TABLE 1-continued

| hsa-miR-17-3p | ACUGCAGUGAAGGCACUUGUAG | SEQ ID NO: 56 |
| --- | --- | --- |
| hsa-miR-193b-5p | CGGGGUUUUGAGGGCGAGAUGA | SEQ ID NO: 57 |
| hsa-let-7i-5p | UGAGGUAGUAGUUUGUGCUGUU | SEQ ID NO: 58 |
| hsa-miR-19b-3p | UGUGCAAAUCCAUGCAAAACUGA | SEQ ID NO: 59 |

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of a miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA), as further described herein below. For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides.

The sequence of the miRNA may be the first 13-33 nucleotides of the pre-miRNA. The sequence of the miRNA may also be the last 13-33 nucleotides of the pre-miRNA.

The miRNA silencing agents of the present invention may comprise nucleic acid analogs that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432: 173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Preparation of miRNAs mimics can be effected by any method known in the art such as chemical synthesis or recombinant methods.

It will be appreciated from the description provided herein above that contacting cells with a miRNA may be effected by transfecting the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Thus, introduction of the miRNAs into the hepatic satellite cells can be effected by:

1. Transiently transfecting the cells with the mature double stranded miRNA;

2. Stably, or transiently transfecting the cells with an expression vector which encodes the mature miRNA.

3. Stably, or transiently transfecting the cells with an expression vector which encodes the pre-miRNA.

4. Stably, or transiently transfecting the cells with an expression vector which encodes the pri-miRNA.

To express miRNAs in the cells, a polynucleotide sequence encoding the miRNA (or pre-miRNA, or pri-miRNA) is preferably ligated into a nucleic acid construct suitable for hepatic cell expression. Such a nucleic acid construct includes a promoter sequence for directing transcription of the polynucleotide sequence in the cell in a constitutive or inducible manner.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example tetracycline-inducible promoter (Zabala M, et al., Cancer Res. 2004, 64(8): 2799-804).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed—i.e. hepatic stellate cells.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

According to one embodiment, a lentiviral vector is used to transfect the hepatic stellate cells.

Various methods can be used to introduce the expression vector of some embodiments of the invention into the cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers. Nanoparticles are also contemplated.

Other modes of transfection that do not involved integration include the use of minicircle DNA vectors or the use of Piggyback transposon that allows the transfection of genes that can be later removed from the genome.

The present inventors contemplate expressing a combination of miRNAs in the cells. For example, at least one, at least two, at least three, at least four, at least five, at least six, at least seven, at least eight, at least nine or at least 10 of the above listed miRNAs may be expressed. In another embodiment, all of the miRNAs listed herein above are expressed.

According to one embodiment, the miRNAs are administered as isolated (i.e. purified) agents—thus, the miRNA composition does not comprise other agents (e.g. proteins, membrane components etc.) which are typically found in hepatic cell-derived exosomes.

The miRNAs of this aspect of the present invention may be administered to the subject using particles.

Exemplary particles that may be used according to this aspect of the present invention include, but are not limited to polymeric particles, microcapsules, liposomes, microspheres, microemulsions, nanoparticles, nanocapsules, nano-spheres, nano-liposomes, nano-emulsions and nanotubes.

According to a particular embodiment, the particles are nanoparticles.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

The particles of this aspect of the present invention may have a charged surface (i.e., positively charged or negatively charged) or a neutral surface.

Agents which are used to fabricate the particles may be selected according to the desired charge required on the outer surface of the particles.

Thus, for example if a negatively charged surface is desired, the particles may be fabricated from negatively charged lipids (i.e. anionic phospholipids) such as described herein below.

When a positively charged surface is desired, the particles may be fabricated from positively charged lipids (i.e. cationic phospholipids), such as described herein below.

As mentioned, non-charged particles are also contemplated by the present invention. Such particles may be fabricated from neutral lipids such as phosphatidylethanolamine or dioleilphosphatidylethanolamine (DOPE).

It will be appreciated that combinations of different lipids may be used to fabricate the particles of the present invention, including a mixture of more than one cationic lipid, a mixture of more than one anionic lipid, a mixture of more than one neutral lipid, a mixture of at least one cationic lipid and at least one anionic lipid, a mixture of at least one cationic lipid and at least one neutral lipid, a mixture of at least one anionic lipid and at least one neutral lipid and additional combinations of the above. In addition, polymer-lipid based formulations may be used.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactie-polyglycolic acid' polyvinyl alcohol, polyvinylpyrrolidone, polymethoxazoline, polyethyloxazoline, polyllydroxyetly-loxazolille, solyhydroxypryloxazoline, polyaspartarllide, polyhydroxypropyl methacrylamide, polymethacrylamide, polydimethylacrylamide, polyvinylmethylether, polyhy-droxyethyl acrylate, derivatized celluloses such as hydroxymethylcellulose or hydroxyethylcellulose.

The polymers may be employed as homopolymers or as block or random copolymers.

The particles may also include other components. Examples of such other components includes, without being limited thereto, fatty alcohols, fatty acids, and/or cholesterol esters or any other pharmaceutically acceptable excipients which may affect the surface charge, the membrane fluidity and assist in the incorporation of the biologically active lipid into the lipid assembly. Examples of sterols include cholesterol, cholesterol hemisuccinate, cholesterol sulfate, or any other derivatives of cholesterol. Preferred lipid assemblies according the invention include either those which form a micelle (typically when the assembly is absent from a lipid matrix) or those which form a liposome (typically, when a lipid matrix is present).

In one embodiment, the particle is a lipid-based nanoparticle. The core of the particle may be hydrophilic or hydrophobic. The core of the lipid-based nanoparticle may comprise some lipids, such that it is not fully hydrophilic.

In a specific embodiment, the particle is a liposome. As used herein and as recognized in the art, liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3): 35-43].

The liposomes may be unilamellar or may be multilamellar. Unilamellar liposomes may be preferred in some instances as they represent a larger surface area per lipid mass. Suitable liposomes in accordance with the invention are preferably non-toxic. The liposomes may be fabricated from a single phospholipid or mixtures of phospholipids. The liposomes may also comprise other lipid materials such as cholesterol. For fabricating liposomes with a negative electrical surface potential, acidic phospho- or sphingo- or other synthetic-lipids may be used. Preferably, the lipids have a high partition coefficient into lipid bilayers and a low desorption rate from the lipid assembly. Exemplary phospholipids that may be used for fabricating liposomes with a negative electrical surface potential include, but are not limited to phosphatidylserine, phosphatidic acid, phosphatidylcholine and phosphatidyl glycerol.

Other negatively charged lipids which are not liposome forming lipids that may be used are sphingolipids such as cerebroside sulfate, and various gangliosides.

The most commonly used and commercially available lipids derivatized into lipopolymers are those based on phosphatidyl ethanolamine (PE), usually distearylphosphatidylethanolamine (DSPE).

The lipid phase of the liposome may comprise a physiologically acceptable liposome forming lipid or a combination of physiologically acceptable liposome forming lipids for medical or veterinarian applications. Liposome-forming lipids are typically those having a glycerol backbone wherein at least one of the hydrofoil groups is substituted with an acyl chain, a phosphate group, a combination or derivatives of same and may contain a chemically reactive group (such as an as amine imine, acids ester, aldehyde or alcohol) at the head group. Typically, the acyl chain is between 12 to about 24 carbon atoms in length, and has varying degrees of saturation being fully, partially or non-hydrogenated lipids. Further, the lipid matrix may be of natural source, semi-synthetic or fully synthetic lipid, and neutral, negatively or positively charged.

According to one embodiment, the lipid phase comprises phospholipids.

The phospholipids may be a glycerophospholipid. Examples of glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC), phosphatidic acid (PA), phosphatidylinositol (PI), phosphatidylserine (PS) and sphingomyelin (SM) and derivatives of the same.

Another group of lipid matrix employed according to the invention includes cationic lipids (monocationic or polycationic lipids). Cationic lipids typically consist of a lipophilic moiety, such as a sterol or the same glycerol backbone to which two acyl or two alkyl, or one acyl and one alkyl chain contribute the hydrophobic region of the amphipathic molecule, to form a lipid having an overall net positive charge.

Preferably, the head groups of the lipid carries the positive charge. Monocationic lipids may include, for example, 1,2-dimyristoyl-3-trimethylammonium propane (DMTAP) 1,2-dioleyloxy-3-(trimethylanino) propane (DOTAP), N-[-1-(2, 3,-ditetradecyloxy)propyl]-N,N-dimethyl-N-hydroxyethyl-ammonium bromide (DMRIE), N-[1-(2,3,-dioleyloxy)pro-pyl]-N,N-dimethyl-N-hydroxy ethyl-ammonium bromide (DORIE), N-[1-(2,3-dioleyloxy) propyl];-N,N,N-trimethyl-ammonium chloride (DOTMA); 3; N—(N',N'-dimethylami-noethane) carbamoly]; cholesterol (DC-Chol), and I dim-ethyl-dioctadecylammonium (DDAB).

Examples of polycationic lipids include a similar lipoplilic moiety as with the mono cationic lipids, to which spermine or spermidine is attached. These include' without being limited thereto, N-[2-[[2,5-bis[3-aminopropyl)ami-no]-1-oxopentyl]amino]ethyl]N,N dimethul-2,3 bis (1-oXo-9-octadecenyl) oXy];-1 propanaminium (DOSPA), and cer-amide carbamoyl spermine (CCS).

The cationic lipids may be used alone, in combination with cholesterol, with neutral phospholipids or other known lipid assembly components. In addition, the cationic lipids may form part of a derivatized phospholipids such as the neutral lipid dioleoylphosphatidyl ethanolamine (DOPE) derivatized with polylysine to form a cationic lipopolymer.

The diameter of the liposomes used preferably ranges from 50-200 nM and more preferably from 20-100 nM. For sizing liposomes, extrusion, homogenization or exposure to ultrasound irradiation may be used, Homogenizers which may be conveniently used include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

According to another embodiment, the particle is a nanoparticle. Preferably, nanoparticles are less than 100 nm in diameter and can be spherical, non-spherical, or polymeric particles. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

The particles of the present invention may be modified. According to one embodiment, the particles are modified to enhance their circulatory half-life (e.g. by PEGylation) to reduce their clearance, to prolong their scavenging timeframe and to allow antibody binding. The PEG which is incorporated into the articles may be characterized by of any of various combinations of chemical composition and/or molecular weight, depending on the application and purpose.

According to a particular embodiment, the particles are coupled to vitamin A—e.g. vitamin A coated liposomes— see for e.g. Sato et al., Nat Biotechnol. 2008 April; 26(4): 431-42.

According to another embodiment, the miRNAs are provided by contacting the cells with particles which are derived (e.g. secreted) from hepatic cells.

Thus, according to another aspect of the present invention there is provided a method of preventing primary hepatic stellate cell differentiation towards a myofibroblast comprising contacting the cells with a particle derived from hepatic cells.

Exemplary hepatic cells from which the particles may be obtained include primary hepatic cells (e.g. primary hepatocytes) or transformed hepatic cells (e.g. HepG2 cell line). Preferably, the hepatic cells are non-diseased hepatic cells.

The term "particle" as used herein refers to a discrete entity that incorporates biological matter such as proteins and/or RNA. It will be appreciated that particle of this aspect of the present invention is not a biological cell.

The particle may be derivable from the hepatic cell by any of several means, for example by secretion, budding or dispersal from the hepatic cells. For example, the particle may be produced, exuded, emitted or shed from the hepatic cell. Where the hepatic cell is in cell culture, the particle may be secreted into the cell culture medium.

The particle may in particular comprise a vesicle. The particle may comprise an exosome. The particles described here may comprise any one or more of the properties of the exosomes described herein.

The particle may comprise a vesicle or a flattened sphere limited by a lipid bilayer. The particles may comprise diameters of 40-100 nm. The particles may be formed by inward budding of the endosomal membrane. The particles may have a density of .about.1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in hepatic cells or hepatic cell conditioned medium (HC-CM), such as a protein characteristic or specific to the hepatic cell or HC-CM. They may comprise RNA, for example miRNA.

According to a particular embodiment, the particle is an exosome.

As used herein, the term "exosome" refers to an extracellular vesicle that is released from a cell upon fusion of a multivesicular body (MVP) with the plasma membrane.

The exosome may (a) have a size of between 50 nm and 100 nm as determined by electron microscopy; (b) comprise a complex of molecular weight >100 kDa, comprising proteins of <100 kDa; (c) comprise a complex of molecular weight >300 kDa, comprising proteins of <300 kDa; (d) comprise a complex of molecular weight >1000 kDa; (e) have a size of between 2 nm and 200 nm, as determined by filtration against a 0.2 pM filter and concentration against a membrane with a molecular weight cut-off of 10 kDa; or (f) have a hydrodynamic radius of below 100 nm, as determined by laser diffraction or dynamic light scattering.

The particle may be something that is isolatable from a hepatic cell or HC-CM. The particle may be responsible for at least an activity of the hepatic cell or HC-CM. The particle may be responsible for, and carry out, substantially most or all of the functions of the hepatic cell or HC-CM. For example, the particle may be a substitute (or biological substitute) for the hepatic cell or HC-CM.

The particle preferably has at least one property of a hepatic cell. The particle may have a biological property, such as a biological activity. The particle may have any of the biological activities of a hepatic cell. The particle may for example have a therapeutic or restorative activity of a hepatic cell.

The particle may be produced or isolated in a number of ways. Such a method may comprise isolating the particle from a hepatic cell. Such a method may comprise isolating the particle from a HC-CM.

The particle may be isolated for example by being separated from non-associated components based on any property of the particle. For example, the particle may be isolated based on molecular weight, size, shape, composition or biological activity.

The conditioned medium may be filtered or concentrated or both during, prior to or subsequent to separation. For example, it may be filtered through a membrane, for example one with a size or molecular weight cut-off. It may be subject to tangential force filtration or ultrafiltration.

For example, filtration with a membrane of a suitable molecular weight or size cutoff, as described in the Assays for Molecular Weight elsewhere in this document, may be used.

The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the particle may be used to track its activity during fractionation of the HC-CM. As an example, light scattering, refractive index, dynamic light scattering or UV-visible detectors may be used to follow the particles. For example, a therapeutic activity such as cardioprotective activity may be used to track the activity during fractionation.

The following paragraphs provide a specific example of how a hepatic cell particle such as an exosome may be obtained.

The hepatic cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6×40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector.

Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of particles in this peak is about 45-55 nm. Such fractions comprise mesenchymal stem cell particles such as exosomes.

The particle may have a size of greater than 2 nm. The particle may have a size of greater than 5 nm, 10 nm, 20 nm, 30 nm, 40 nm or 50 nm. The particle may have a size of greater than 100 nm, such as greater than 150 nm. The particle may have a size of substantially 200 nm or greater.

The particle or particles may have a range of sizes, such as between 2 nm to 20 nm, 2 nm to 50 nm, 2 nm to 100 nm, 2 nm to 150 nm or 2 nm to 200 nm. The particle or particles may have a size between 20 nm to 50 nm, 20 nm to 100 nm, 20 nm to 150 nm or 20 nm to 200 nm. The particle or particles may have a size between 50 nm to 100 nm, 50 nm to 150 nm or 50 nm to 200 nm. The particle or particles may have a size between 100 nm to 150 nm or 100 nm to 200 nm. The particle or particles may have a size between 150 nm to 200 nm.

The size may be determined by various means. In principle, the size may be determined by size fractionation and filtration through a membrane with the relevant size cut-off. The particle size may then be determined by tracking segregation of component proteins with SDS-PAGE or by a biological assay.

The size may comprise a hydrodynamic radius. The hydrodynamic radius of the particle may be below 100 nm. It may be between about 30 nm and about 70 nm. The hydrodynamic radius may be between about 40 nm and about 60 nm, such as between about 45 nm and about 55 nm. The hydrodynamic radius may be about 50 nm.

The hydrodynamic radius of the particle may be determined by any suitable means, for example, laser diffraction or dynamic light scattering.

The particle may comprise one or more proteins or polynucleotides secreted by a hepatic cell. The particle may comprise one or more proteins or polynucleotides present in HS-CM. In a particular embodiment, the particle may comprise miRNAs which are derived from hepatic cells.

For example, the particle may comprise 10% or more, 20% or more, 30% or more, 40% or more, 50% or more, 60% or more or 70% or more of these proteins and/or polynucleotides. The particle may comprise substantially about 75% of these proteins and/or polynucleotides. The proteins may be defined by reference to a list of proteins or gene products of a list of genes.

The cells of this aspect of the present invention may be in a cell culture (i.e. propagated in a culture medium).

A particular method of culturing hepatic stellate cells is described in the Examples section herein below.

The miRNA agents or particles described herein may be tested (or corroborated) as anti-fibrotic agents using in-vitro culturing assays, as further described herein below.

Additionally, or alternatively, the miRNA agents or particles described herein may be tested using animal models.

One such mouse model is the CCL4 mouse model. An exemplary experiment for testing the agents is as follows: mice may be injected twice a week for 4 weeks with CCL4 (ml/kg). 24 hours after the last injection, mice may be injected I.V. with exosomes purified from medium collected from either primary hepatocytes or hepatoma cell line grown in tissue culture for 7 days. Another group of mice may be injected with miRNAs purified from the hepatocytes exosomes. The mice may be treated with CCL4 for additional 4 weeks. Mice will be than sacrificed 1,2,3 and 4 weeks after the injection. As a control, mice may be treated the same with CCL4 but injected with either exosomes or miRNA purified from the exosomes collected from a non-hepatic cell medium. 1,2,3 and 4 weeks after the exosomes/miRNA injection, liver samples may be collected for pathological examination including staining for Masson's trichrome and anti-αSMA. Furthermore, liver enzymes levels may be tested in the serum of these mice as markers for the levels of hepatic fibrosis.

Other animal models which may be used to test the agents are described in Delire B, et al., J Clin Transl Hepatol. 2015 March; 3(1):53-66; Moore B, Am J Respir Cell Mol Biol. 2013 August; 49(2):167-79; (lung fibrosis model); Ishikawa K, Exp Eye Res. 2016 January; 142:19-25 (eye fibrosis model); Nogueira A, In Vivo. 2017 Jan. 2; 31(1):1-22 (renal fibrosis model); Rai V et al., Mol Cell Biochem. 2017 January; 424(1-2):123-145 (Cardiac fibrosis model); and Reed A, Exocrine Pancreas Knowledge Base 2014 (pancreatic fibrosis model).

In one embodiment, the miRNAs or particles described herein are administered in vivo to a subject.

Thus, according to another aspect of the present invention the miRNAs or particles described herein are provided to a subject in order to treat a fibrotic disease.

The term "fibrosis" refers to the formation of fibrous tissue or "fibrotic tissue", usually as a reparative or a reactive process.

Fibrosis may occur in any organ including, for example, kidney, lung, liver, skin, central nervous system, bone, bone marrow, cardiovascular system, an endocrine organ or the gastrointestinal system. By "fibrosis-associated condition" is meant any condition that is related to fibrosis. Thus, fibrosis-associated conditions may be caused by, be concomitant with, or cause fibrosis.

Examples of pathologic and excessive fibrotic accumulations include, but are not limited to, pulmonary fibrosis, asthma, adult respiratory distress syndrome (ARDS), chronic obstructive pulmonary disease (COPD), idiopathic pulmonary fibrosis (IPF), acute lung injury (ALI), pulmonary fibrosis due to infectious or toxic agents, such as radiation therapy or chemotherapy, pulmonary fibrosis due to particle inhalation, post-transplant pulmonary fibrosis, perirenal fascitis, glomerulonephritis (GN), diabetic nephropathy, renal interstitial fibrosis, renal fibrosis resulting from complications of drug exposure, HIV-associated nephropathy, transplant necropathy, retroperitoneal fibrosis, perivascular fibrosis in Systemic Lupus Erythematosus (SLE), obstruction-induced fibrosis in kidneys or spleen, benign prostate hypertrophy, fibrocystic breast disease, uterine fibroids, ovarian cysts, endometriosis, coronary infarcts, myocardial fibrosis, cerebral infarcts, congestive heart failure, dilated cardiomyopathy, myocarditis, myelofibrosis, vascular stenosis, progressive systemic sclerosis, polymyositis, scleroderma (which affects the skin and the lungs), dermatomyositis, Raynaud's syndrome, retroperitoneal fibrosis, progressive massive fibrosis, nephrogenic systemic fibrosis, Crohn's disease, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, rheumatoid arthritis, musculoskeletal fibrosis, post-surgical adhesions, liver fibrosis, autoimmune hepatitis, cirrhosis including primary biliary cirrhosis, viral hepatitis including HIV- or Hepatitis C-induced hepatitis, real fibrotic disease, fibrotic vascular disease, e.g., atherosclerosis, varix, or varicose veins, scleroderma, Alzheimer's disease, diabetic retinopathy, glaucoma, proliferative vitreoretinopathy, fibrosis associated with ocular surgery, chronic transplant rejection, graft vs. host disease, radiation-induced fibrosis, and excessive or hypertrophic scar and/or keloid formation in the dermis occurring during wound healing resulting from trauma or surgical wounds.

In one embodiment, the disorder to be treated is a disorder that results in fibrosis or sclerosis, including but not limited to groups of disorders selected from skeletal muscle fibrosis, irradiation-induced fibrosis, autoimmune-related fibrosis, cardiovascular fibrosis, arteriosclerotic disorders, pulmonary fibrosis, adult respiratory distress syndrome, inflammatory disorders, scleroderma, cirrhosis, keloids, adhesions, hypertrophic scars; skeletal muscle fibrosis associated with a condition, such as muscular dystrophy, denervation atrophy induced by neuromuscular disease, or traumatic injury-induced denervation atrophy; cardiovascular fibrosis selected from left ventricular hypertrophy secondary to hypertension, fibrosis associated with myocardial infarction, fibrosis associated with ischemiareperfusion injury, or fibrosis associated with myocarditis; dermal fibrosis, keloid formation, hypertrophic scar formation, or adhesion formation; pulmonary fibrosis, pulmonary fibrosis due to adult respiratory distress syndrome and irradiation induced fibrosis, or a combination thereof.

In some embodiments, the fibrosis is a localized type of fibrosis, such as for example, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, carpal tunnel syndrome, tarsal tunnel syndrome or a combination thereof. Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation, Acute promyelocytic leukemia, Acute nonlymphocytic leukemia with increased basophils, Acute monocytic leukemia, Acute myelomonocytic leukemia with eosinophilia; Malignant lymphoma, such as Birkitt's Non-Hodgkin's; Lymphocytic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

In one embodiment, the disease is a hepatic disease such as hepatitis, an autoimmune hepatic disease, alcoholic steatohepatitis (ASH) and non-alcoholic steatohepatitis (NASH).

The active agents described herein (e.g. at least one of the miRNAs, particles derived from hepatic cells, such as exosomes, or hepatic cell conditioned medium) may be provided to the subject per se or as part of a pharmaceutical composition.

As used herein a "pharmaceutical composition" refers to a preparation of one or more of the agents described herein, with other chemical components such as pharmaceutically suitable carriers and excipients. The purpose of a pharmaceutical composition is to facilitate administration of the agent to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body (e.g. the liver).

A recombinant vector can be administered in several ways. If vectors are used which comprise cell specific promoters, for example, the procedure can take advantage of their target specificity and consequently, do not have to be administered locally at the diseased site.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans. Exemplary models for fibrosis have been described herein above.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively treat disorder. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

As mentioned, herein above, the present inventors contemplate screening for new agents which are useful for treating a disease associated with fibrosis by analyzing if the agent is capable of preventing differentiation of primary hepatic stellate cells towards a myofibroblast.

Methods of culturing primary hepatic stellate cells are described in the examples section herein below and herein above.

Exemplary markers indicative of differentiation include, but are not limited to αSMA or Col1A. Other contemplated markers include PDGF, TGFβ, TIMP1 and/or TIMP2. An increase in such markers is indicative of differentiation. Alternatively, or additionally, the analysis may be performed by visualizing the cells under a microscope. A dye or stain may be used to aid in visualization such as Oil Red O staining.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Subjects that may be treated are typically mammalian subjects such as humans, rodents, monkeys, dogs, cats, horses etc.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Primary hepatic stellate cell isolation: Livers were dissected and washed using Gey's balanced salt solution (GBSS) as buffer. The livers were incubated in a 37° C. bath with GBSS200 (GBSS, supplemented with collagenase (Enco), pronase (Dyn Diagnostics) and CaCl2), for 15 minutes. GBSS100 (GBSS, supplemented with collagenase (Enco), pronase (Dyn Diagnostics), CaCl2 and DNase I (Sigma)) was then added to the suspended cells for 30 minutes. Afterwards, the liver extract was filtered through a steel net and divided into 50 ml tubes and centrifuged at room temperature (2000 rpm, 7 min). The supernatant was discarded and the pellet was suspended in 7 ml OptiPrep™ (Sigma) diluted in GBSS (1:6). After the pellet was suspended, an additional volume of GBSS buffer (5 ml) was slowly added. The tubes were centrifuged (room temperature, 14,000 rpm, 20 min, without break). The HSC layer was collected to a new tube and 20 ml DMEM were added. The cells were then centrifuged (room temperature, 2000 rpm, 7 min), the supernatant was discarded and the pellet was washed again with 20 ml DMEM. The pellet was re-suspended in 10 ml 10% FBS DMEM, to a cell density of $4*10^6$ cells/ml. Cells were cultured in DMEM, supplemented with 10% FBS, 1% penicillin: streptomycin and 1% glutamine, at 37° C., in a humidified incubator with 5% $CO_2$.

RNA extraction and reverse transcription: Total RNA was extracted from cells using the TRI Reagent™ (Sigma), according to the manufacturer's protocol. RNA concentration was determined with the NanoDrop spectrophotometer (Thermo Scientific). cDNA was prepared by reverse transcription (High Capacity cDNA Reverse Transcription Kit, Applied Biosystems) of 2 µg total RNA, according to the manufacturer's instructions.

qRT-PCR: Quantitative real-time polymerase chain reaction was performed using Fast SYBR™ Green PCR Master Mix (Applied Biosystems), with the specific primers and probes listed in Table 2. The reaction was performed with the Applied Biosystems StepOne™ Real-Time PCR System. The relative quantification of mRNA analyses were performed using the ΔΔCT method (comparative ΔCT), 18S as the internal control gene for normalization. Each reaction was performed in triplicates and each experiment was performed at least three times.

TABLE 2

Sequences of primers used in this study
(F-forward; R- reverse)

| | Forward | Reverse |
|---|---|---|
| m Col1a | ACTGGAAGAGCGGAGAGTAC SEQ ID NO: 1 | GCACAGACGGCTGAGTAG SEQ ID NO: 2 |
| m αSMA | CTGCCGAGCGTGAGATTG SEQ ID NO: 3 | AGGCAGTTCGTAGCTCTTCT SEQ ID NO: 4 |
| m 18S | ACCCGTTGAACCCCATT SEQ ID NO: 5 | TCCAATCGGTAGTAGCG SEQ ID NO: 6 |

Protein extraction: Proteins were extracted from cells using RIPA buffer (Sigma), supplemented with protease inhibitor (Roche) and phosphatase inhibitor cocktail 2 and 3 (Sigma), followed by quantification using the BCA kit (Pierce), according to the manufacturer's protocol.

Western blotting: Proteins were separated on a 10% SDS gel, and then transferred to nitrocellulose membranes (Whatman). The membranes were probed with anti-αSMA monoclonal antibody (1:1000) (Sigma Aldrich), followed by incubation with an HRP-conjugated secondary antibody (1:10,000) (Jackson ImmunoResearch) and later with ECL chemiluminescent substrate (Pierce Waltham). Relative quantification of the proteins was performed using the Image J software.

In vivo model: Mice were injected with either CCL4 (ml/kg) dissolve in olive oil or olive oil alone twice a week for 4 weeks. 24 hours after the last injection, exosomes secreted from either HepG2 or LX2 ($1.5*10^9$) were introduced IV to the mice. Mice were injected with additional doses of CCL4 for the next 2 weeks and then they were sacrificed (scheme of the in-vivo model protocol is presented in FIG. 18).

Administration of exosomes: Animals were treated with $1.5\times10^9$ particles of LX2 or HepG2 exosomes dissolved in 200 µl PBS, injected into the tail vein. Negative controls were injected with 200 µl PBS.

Measurement of liver enzymes: Serum aspartate transaminase (AST) and alanine transaminase (ALT) levels were determined using AU5800 from BECKMAN COULTER, by standard procedures.

Results

Using the protocol described herein above, a primary culture of isolated HSCs was generated, (FIGS. 1A-B). Unlike HSC lines, which are partially differentiated, primary HSCs are undifferentiated, therefore, their activation in vitro mimics reliably in vivo events. The transformation of HSCs from vitamin A—storing cell (FIG. 1C) to a myofibroblast-like cell (FIG. 1D) was visualized using Oil Red O staining. Both αSMA and Col1A RNA expression level increased in the activated primary HSCs compared to the non-active cells (FIG. 1E), indicating differentiation to myofibroblast-like cells.

Figure 2A:
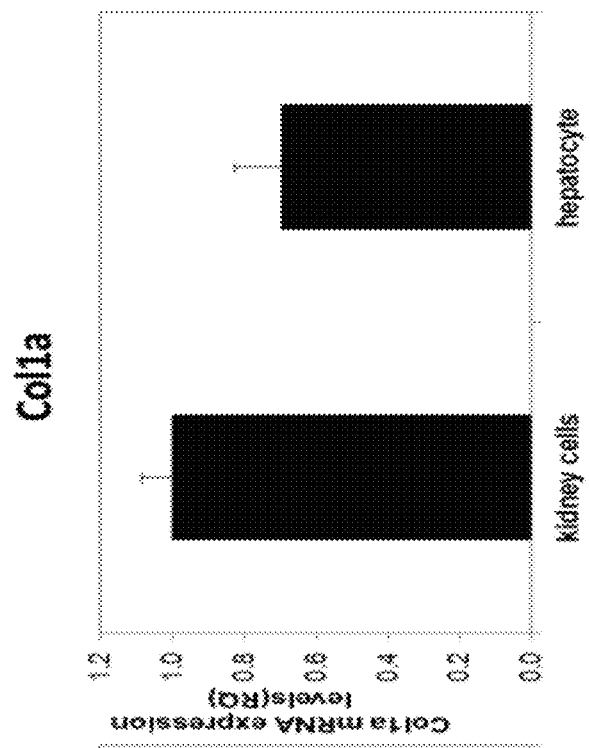
FIGS. 2A-B: Hepatocyte medium inhibits HSC activation. Primary hepatocytes and kidney cells were grown in 2% FCS+DMEM for 5 days. The media were then collected and added to primary HSCs isolated from mouse liver. αSMA (FIG. 2A) and Col1A (FIG. 2B) expression level in the HSCs was evaluated after 24 h using qRT-PCR.
Figure 2B:
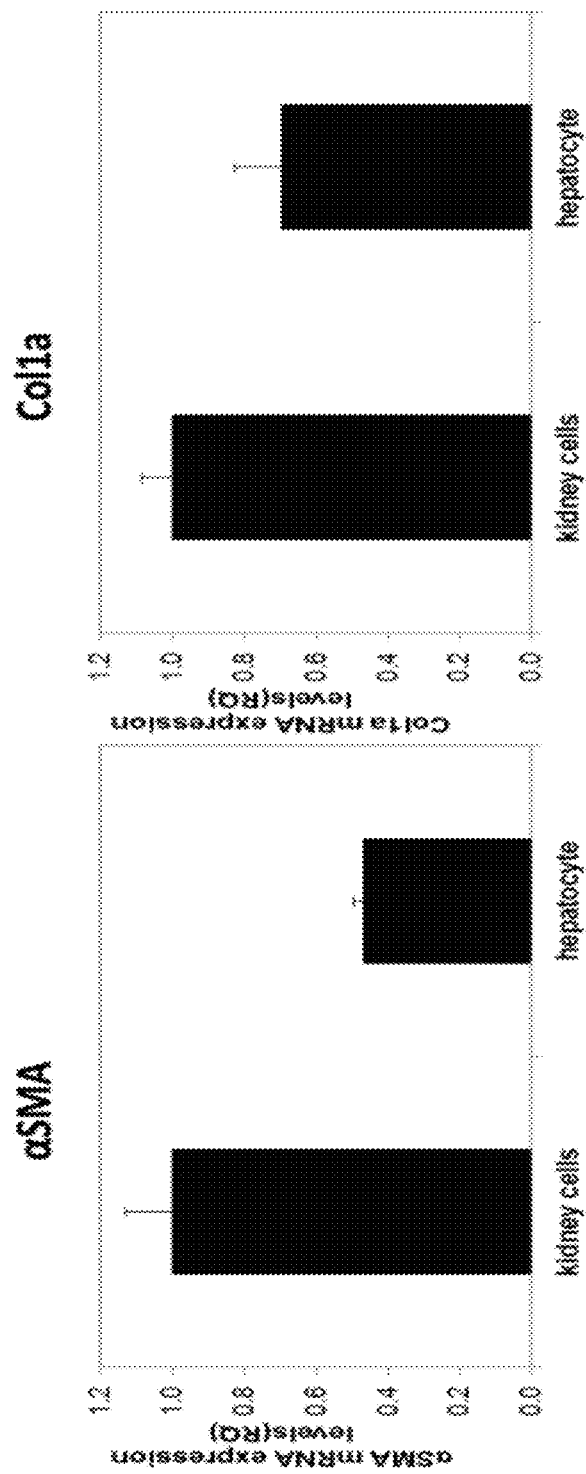

Primary hepatocytes or primary kidney cells were isolated from C57BL6 mice in order to investigate the direct effect of primary hepatocytes on the steady state level of the HSCs. 5 days after isolation, medium from these cells was collected and added to primary HSCs. 24 hours later RNA was purified from the HSCs and the level of αSMA and Col1A (markers of HSCs activation) was quantified by qRT-PCR. The expression level of both αSMA and Col1A was lower in HSCs that were incubated in medium collected from primary hepatocytes as compared to the same cells incubated in medium collected from primary kidney cells (αSMA p=0.018 Col1a p=0.07) (FIGS. 2A-B). These results suggest that medium from primary hepatocytes can directly inhibit HSC activation and therefore might inhibit the development of fibrosis.

Figure 3A:
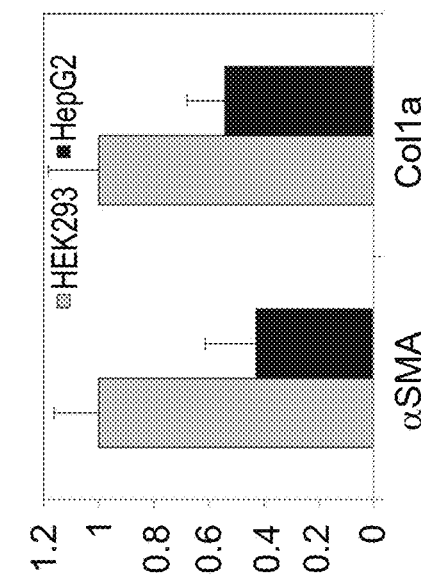
FIGS. 3A-C: Hepatocyte and hepatoma cell line media inhibit HSCs activation. Hepatocytes and kidney cells (primary or cell line, respectively) or LX2 (HSC cell line) were grown in 2% FCS+DMEM for 5 days. The media were then collected and added to primary HSCs isolated from mouse liver. αSMA and Col1A expression level in the HSCs were evaluated after 24 h using qRT-PCR.
Figure 3B:
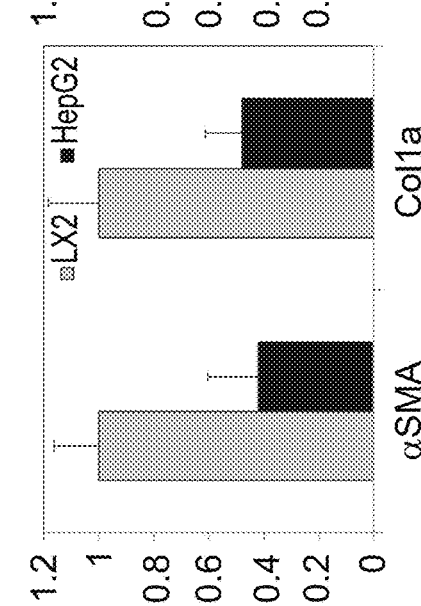
Figure 3C:
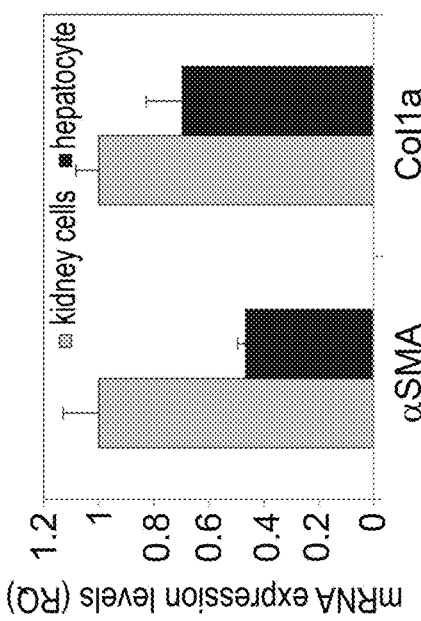

Similar experiments were performed using medium collected either from a hepatoma cell line (HepG2), HSCs line (LX2) (FIG. 3B) and a kidney cells line (HEK) (FIG. 3C). Only medium collected from hepatocytes can inhibit the activation of primary HSCs.

Figure 4B:
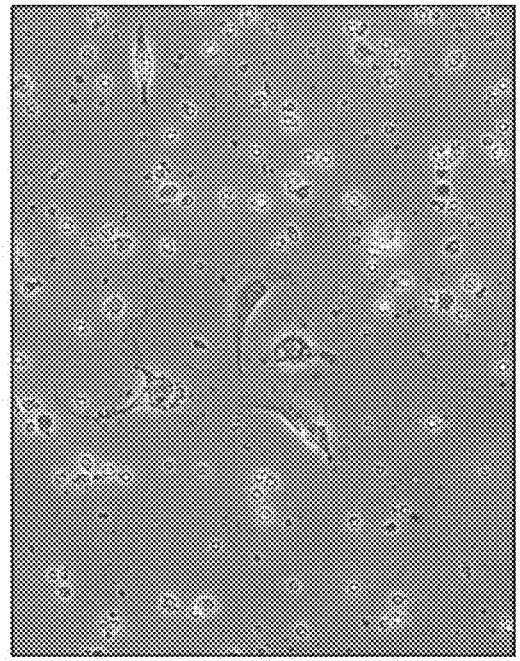
FIGS. 4A-B: Phenotypic changes in HSCs treated with either LX2 or HepG2-conditioned medium. HSCs were isolated from mouse liver and grown for 4 days in either HepG2- or LX2-conditioned medium. Photos were taken using inverted microscope.
Figure 4A:
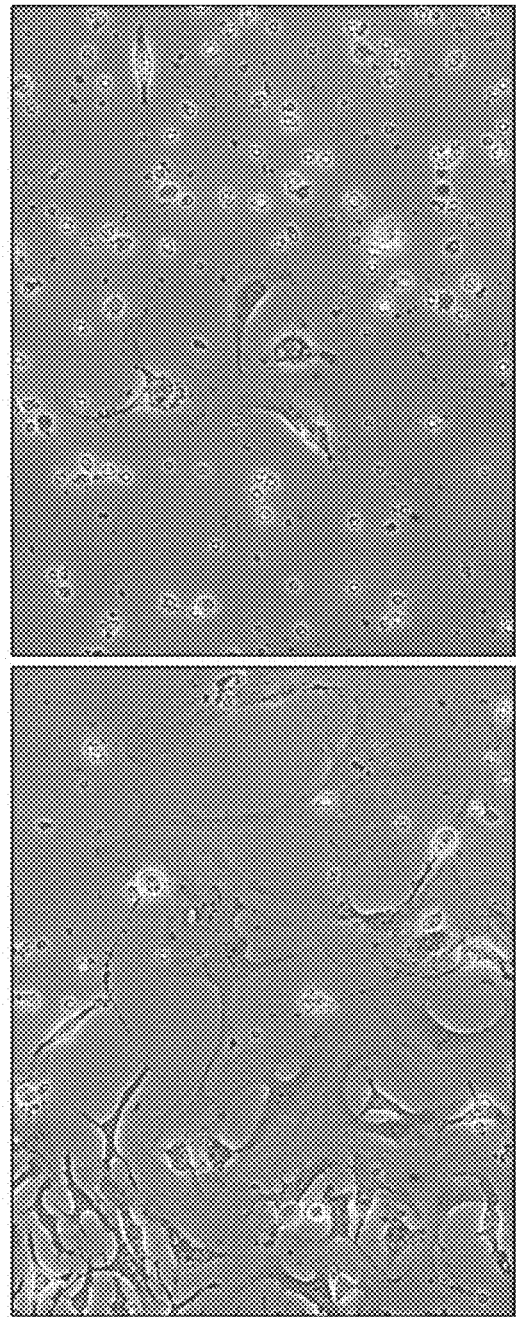

To further establish the effect of different medium on the activation of primary HSC, the cells were incubated in medium collected from hepatocytes or medium collected from other cells for 4 days whilst following their phenotypical changes. As can be seen in FIGS. 4A-B, HSCs treated with LX2 medium displayed differentiation characteristics, while the same cells treated with medium from HepG2 cells exhibited undifferented phenotype (FIGS. 4A-B).

Figure 5:
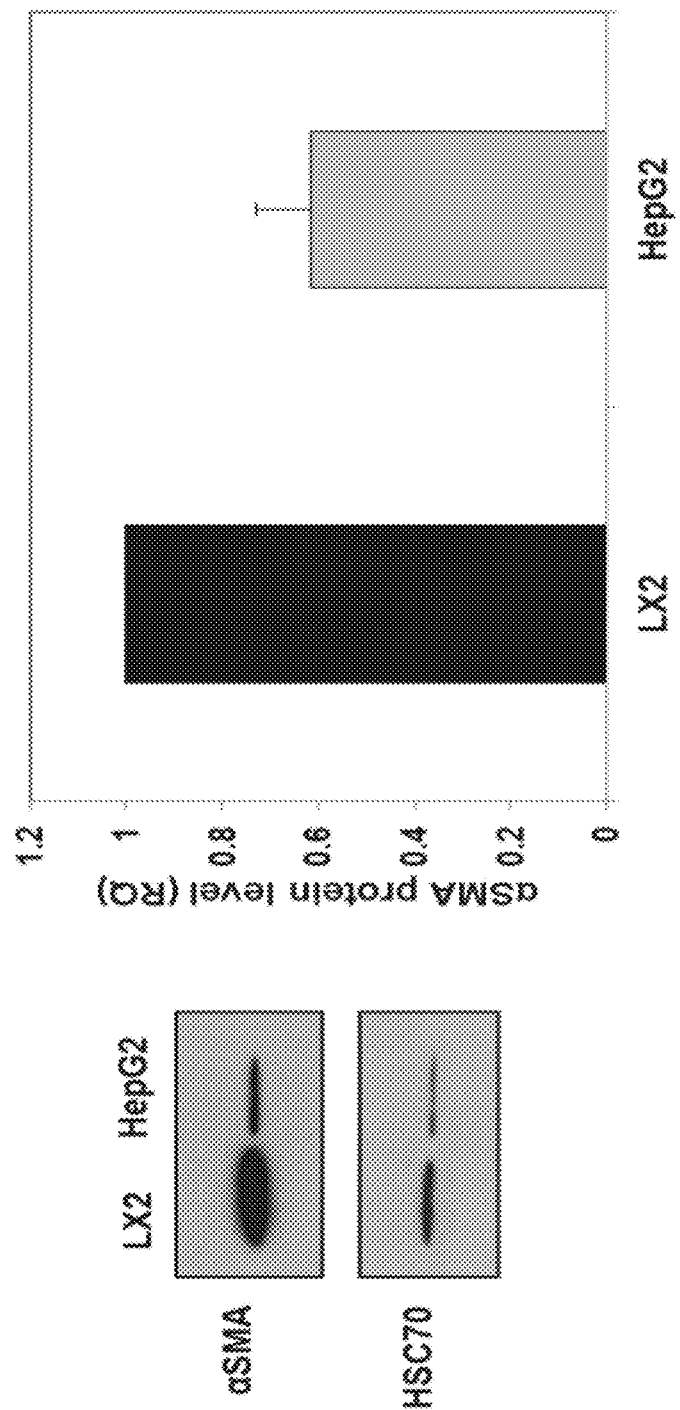
FIG. 5: Hepatocyte-conditioned medium inhibits the activation of HSCs. HepG2 or LX2 cells were grown in 2% FCS+DMEM for 5 days. The medium was then collected and added to primary HSCs isolated from mouse liver. After 24 hrs, cells were harvested and the levels of the αSMA protein were assessed using Western blot analysis.

Additionally, αSMA protein levels in cells treated with LX2-conditioned medium was higher than in HSCs treated with HepG2-conditioned medium (FIG. 5).

All of these results demonstrated that medium from hepatocytes can inhibit the spontaneous activation of primary HSCs.

Since fibrosis is a reversible process, the present inventors examined the effect of hepatocytes on HSCs that have already started the activation process. Primary HSCs were cultured in 10% FCS/DMEM medium and went through spontaneous activation. After 7 days, their medium was changed to either primary hepatocyte-conditioned medium or kidney cell-conditioned medium. After an additional 7 days in culture, the level of HSCs activation was assessed by quantifying αSMA and Col1A transcripts using qRT-PCR. The same experiment was also performed with medium collected either from the HepG2 or the LX2 cell line. The medium from primary hepatocytes or the hepatoma cell line reversed the HSC transdifferentiation, while medium from primary kidney cells and LX2 cell line did not induce differentiation (FIGS. 6A-B). These findings suggest that hepatocyte-conditioned medium can directly reverse the fibrosis process.

Figure 7A:
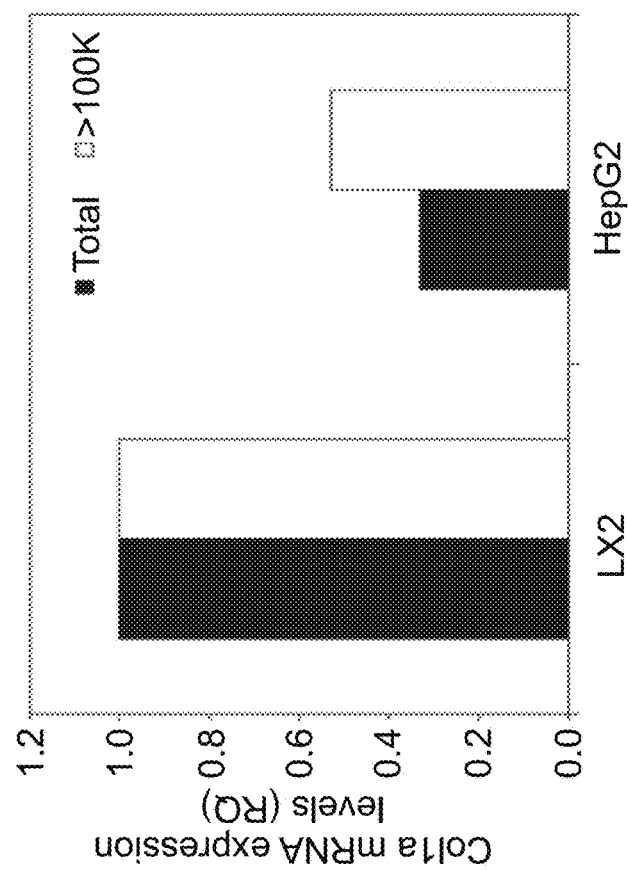
FIGS. 7A-B: HepG2 cell medium fractions higher than 100 kDa inhibit the activation of primary HSCs. Media from HepG2 and LX2 cells were collected and separated through a cellulose membrane with a cutoff of 100 kDa. Primary HSCs were grown in the higher than 100 kDa fractions or in the whole medium. HSC activation level was determined by the levels of αSMA and Col1A expression after 24 h.
Figure 7B:
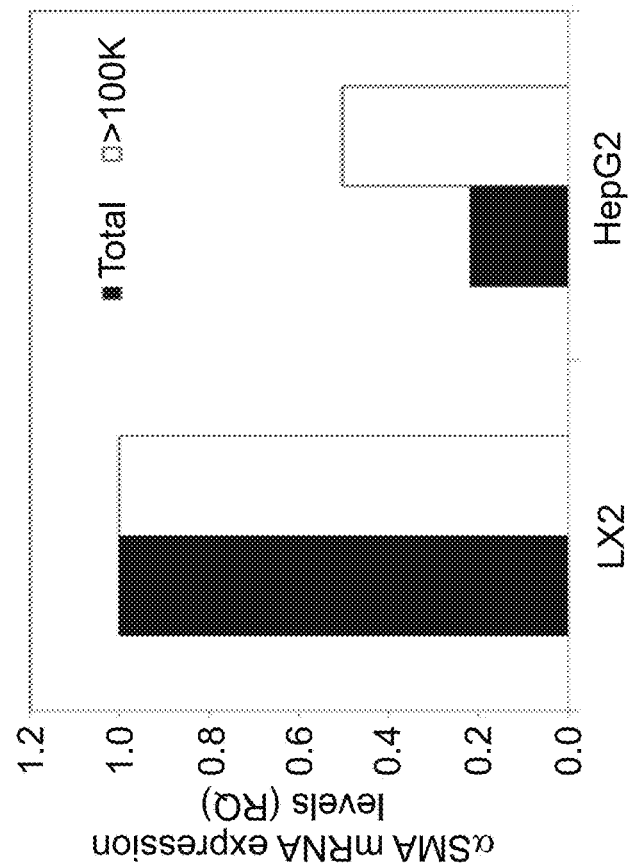

In order to characterize the factor/s that are secreted to the medium and inhibit HSCs activation, the HepG2 cell-conditioned media was fractionated using a cellulose membrane, which can separate between molecules larger or smaller than 100 kDa. Using this assay it was shown that the fraction that contain the large particles (>100 kDa) can inhibit the activation of the primary HSCs (FIGS. 7A-B).

Figure 8:
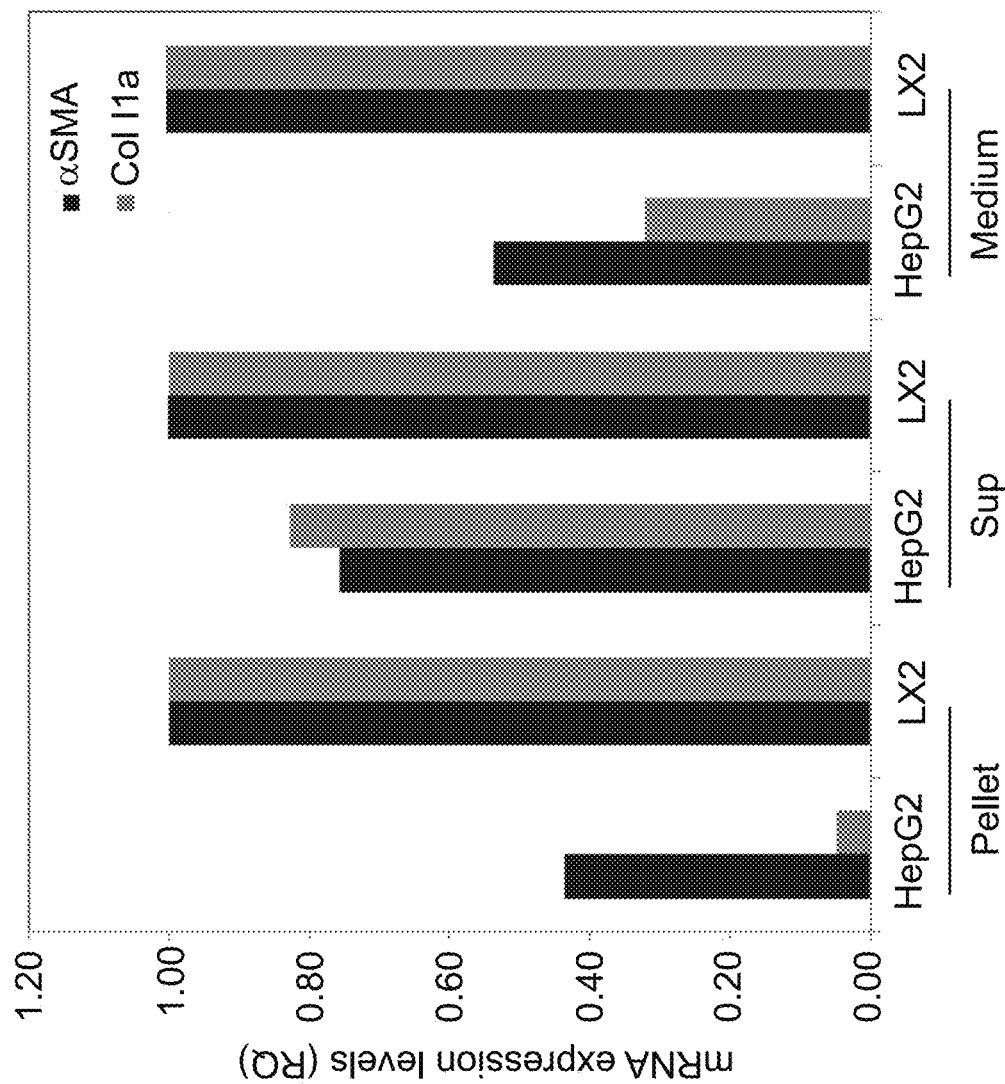
FIG. 8: Pellets of HepG2 medium can inhibit HSC activation. Primary HSCs were incubated in the presence HepG2 or LX2 purified exosomes. 24 hours later the levels of αSMA and Col1A were measured using RT-qPCR.

To further identify the particles responsible for the inhibition of HSCs, the HepG2 medium was separated into two fractions of pellet and supernatant using an ultracentrifuge. When HSCs were incubated with the pellet of the HepG2 for 24 hours, inhibition of HSC stimulation was found (FIG. 8).

Figure 9B:
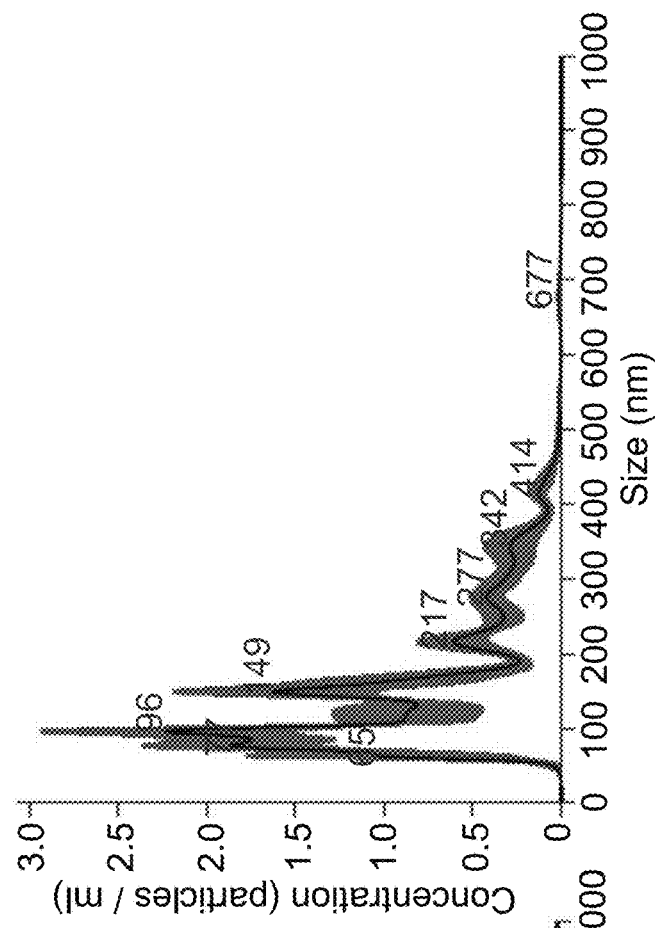
FIGS. 9A-B: Particles size in the HepG2 and LX2 mediums pellets are around 100 nM. The pellets of the cells were subjected to Nanostream analysis.
Figure 9A:
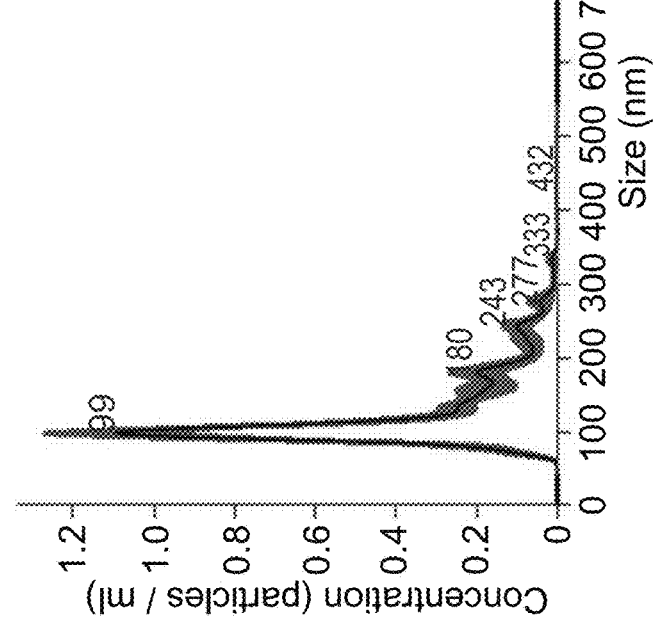
Figure 10B:
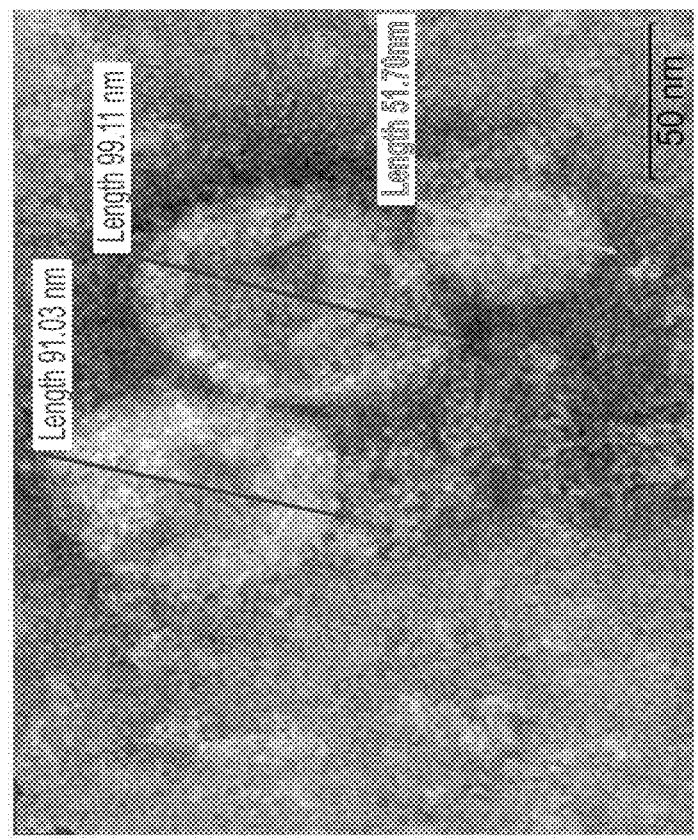
FIGS. 10A-B: TEM pictures of HepG2 secreted particles.
Figure 10A:
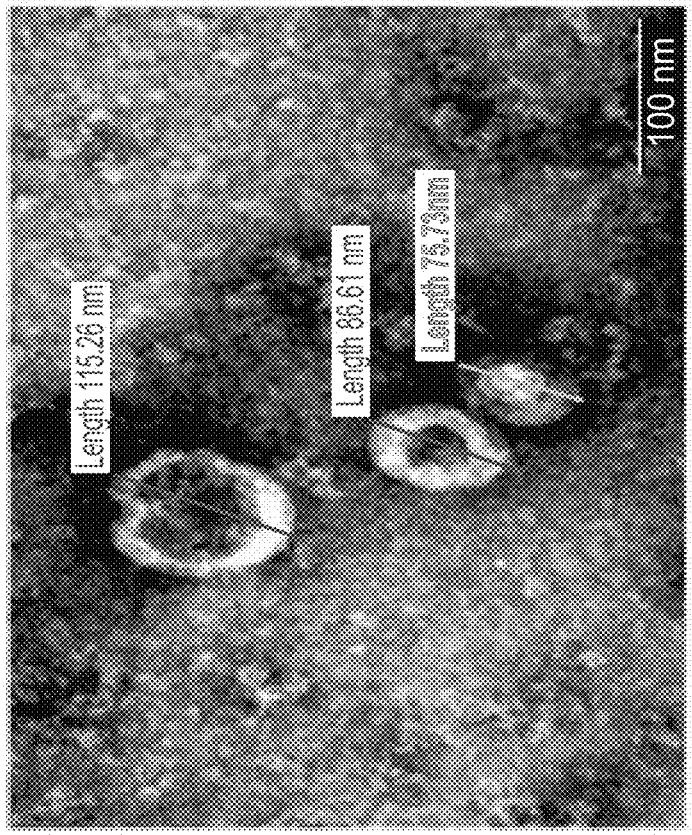

To examine the content of the HepG2 medium pellet, a nanosight analyzer was used. As illustrated in FIGS. 9A-B, most of the particles in the pellet are around 100 nm. These results were validated using TEM (transmission electron microscopy) (FIGS. 10A-B).

Exosomes are extracellular vesicles, which are known to provide a means of intercellular communication and of transmission of macromolecules including miRNAs between cells). Furthermore, exosomes size is usually around 100 nm. Based on the size of the particles found in the HepG2 medium (~100 nM) and their role in cell to cell communication, the present inventors hypothesized that the inhibition of HSCs by the hepatocytes is mediated by exosomes.

Figure 11:
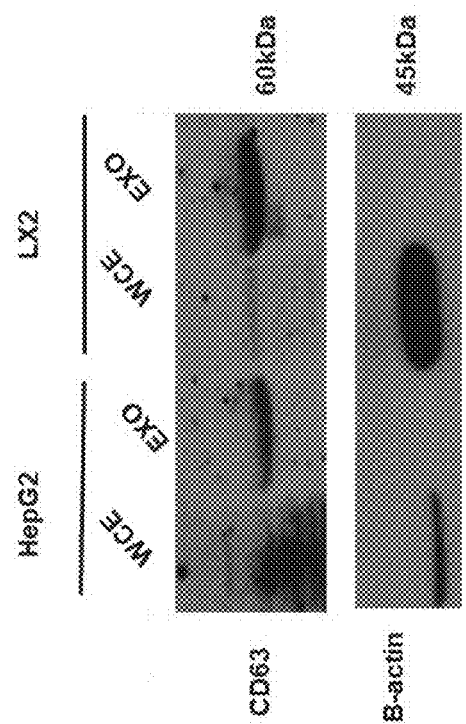
FIG. 11: The pellets of both HepG2 and LX2 cells contain exosomes. The pellets was purified from HepG2 and LX2 cells medium using ultra-centrifugation. Proteins were extracted from the mediums pellet and the presence of CD630 protein marker was evaluated using specific antibodies.

CD63 is a protein which is abundant on the exosome surface and serves as a marker for the presence of these particles. To examine the presence of exosomes in the pellet of the cells, the present inventors analyzed the presence of CD63 using Western blot analysis. Using the anti-CD63 antibodies it was shown that the HepG2 and LX2 medium pellet contain exosomes (FIG. 11).

Figure 12:
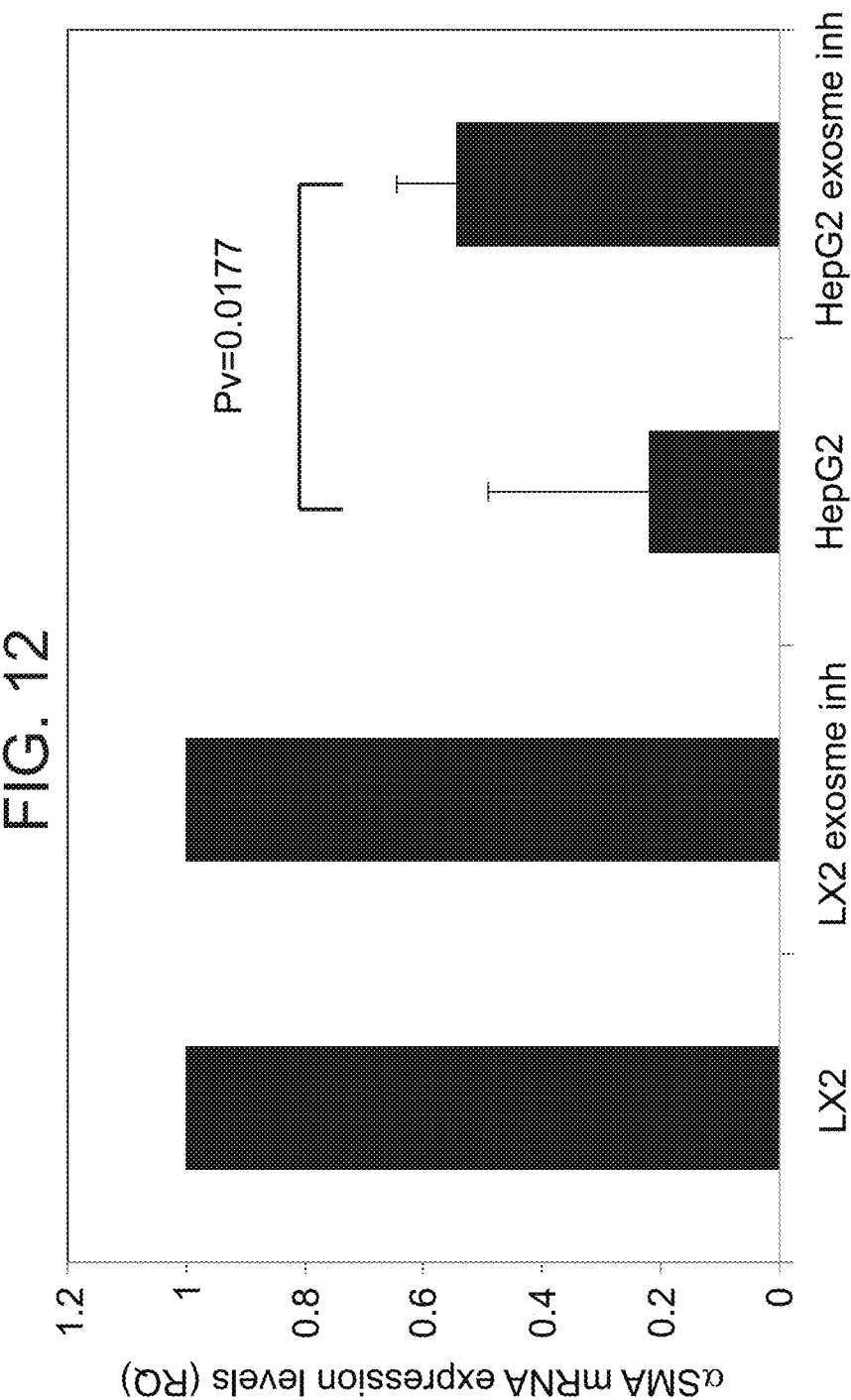
FIG. 12: Inhibition of exosomes secretion attenuate the activity of HepG2 cells medium on HSCs. HepG2 and LX2 cells were treated with 20 μM of GW4869 (inhibitor of exosome secretion) for 5 days. The media of the cells were then collected and added to primary HSCs isolated from mouse liver. αSMA expression level in the HSCs was evaluated after 24 h using qRT-PCR.

To validate that the active components in the HepG2 mediums are exosomes, the secretion of the exosomes from the HepG2 and LX2 cells was inhibited. Primary HSCs were treated with either medium of untreated HepG2 or LX2 or medium of these cells treated in order to prevent exosome secretion. HSC activation levels were measured using αSMA and Col1A expression. These experiments demonstrated that medium from HepG2 cells that do not contain the exosome have significantly lower ability to inhibit the HSCs stimulation compared to medium from un-treated HepG2 cells (FIG. 12).

Figure 13:
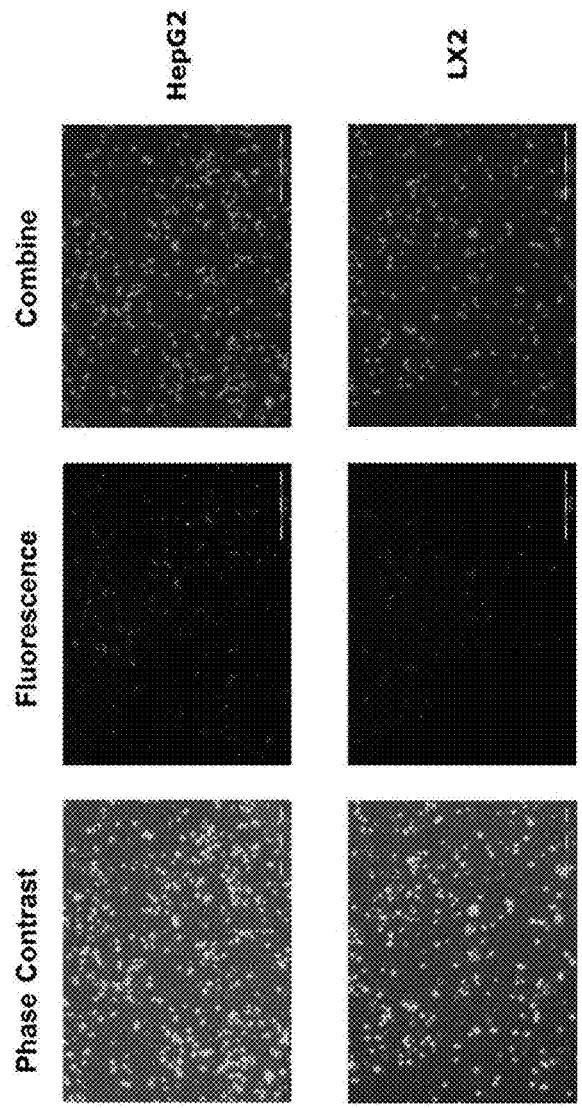
FIG. 13: Purified exosomes secreted from HepG2 and LX2 can communicate with primary HSCs. Purified exosomes from HepG2 and LX2 cells were dyed with triazole orange. Primary HSCs were incubated with the dyed exosomes for 15 minutes at 37° C. Cells were washed from the excess exosomes and pictures were taken using fluorescence microscopy.

To examine the functionality of the purified exosomes, the exosomal RNA were dyed using Triazole orange. Then the primary HSCs were incubated with the indicated exosomes for 15 minutes. The cells were washed from the excess of the exosomes and analyzed using fluorescence microscopy. As can be seen in FIG. 13, most of the HSCs contain RNA-dyed with triazole orange. This result indicates that the purified exosomes are active and they can transfer their RNA molecules into the HSCs (FIG. 13).

To determine that the RNA molecules are the active component in the exosomes, the RNA molecules were purified from the exosome and transfected into primary HSCs. 48 hours later, the cells were harvested and the stimulation levels of the HSCs was analyzed. HSCs transfected with RNA purified from the HepG2 secreted exosomes showed inhibition of stimulation compared to the same cells transfected with RNA purified from LX2 secreted exosomes (FIG. 14).

Figure 17:
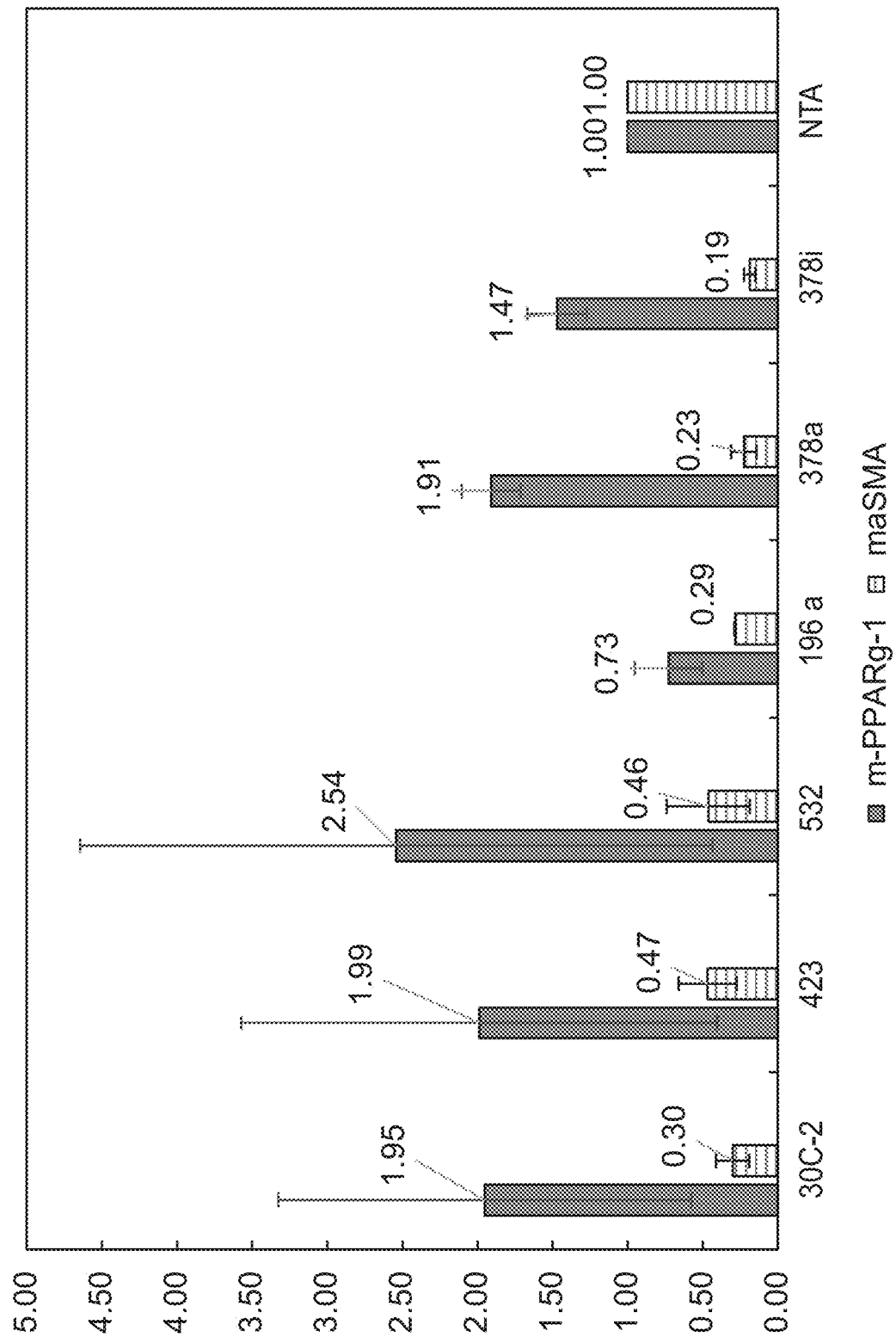
FIG. 17: miRNA mimics found in HepG2 exosomes can inhibit primary HSCs activation. Primary HSCs were transfected with 70 pmol of the miRNA mimics. 48 hours later the cells were harvested and the levels of αSMA and PPRγ-1 expression were measured using RT-qPCR.

In order to discover which miRNA molecules are present in the HepG2 but not in the LX2 secreted exosomes, the miRNAs from HepG2 and LX2 secreted exosomes were purified and sent to RNAseq. 23 miRNAs showed significant higher expression in the HepG2 compare to LX2 secreted exosomes (FIG. 15).

miRNA mimics of miR-196, miR378a and miR-378i were transfected into the primary HSCs. As a control, non-relevant siRNA was used. 48 hours later, these cells were harvested and the levels of stimulation were measured by the expression of αSMA and Col1a. The results of this experiment showed that all three miRNAs have the ability to inhibit HSC stimulation (FIG. 16). Additional miRNA mimics including miR-30c-2-3p, miR-423-5p and miR-532-5p were also shown to inhibit HSC stimulation (FIG. 17).

Inhibition activity of combinations of several miRNA molecules were analyzed. Higher levels of HSC inhibition was observed as compared to these miRNAs alone. The combinations of either miRNA-423-5p and miRNA-532-5p or miRNA-30c-2-3p and miRNA-532-5p led to >90% inhibition of HSC activation (FIG. 19).

In order to evaluate the ability of medium collected from primary hepatocytes to inhibit the development of fibrosis, a well-known in-vivo model for liver fibrosis was established using CCL4.

Figure 20A:
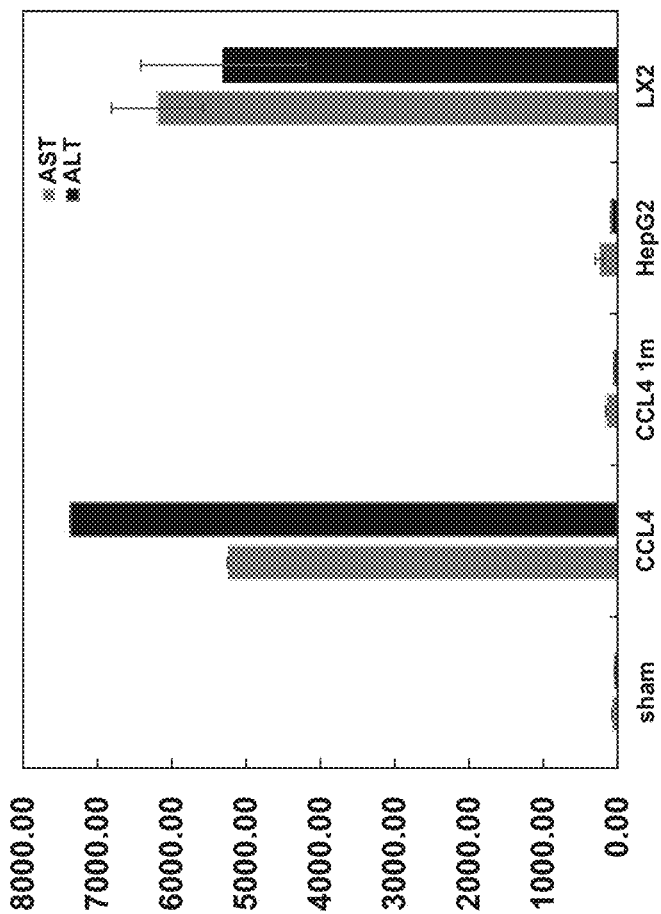
Figure 20B:
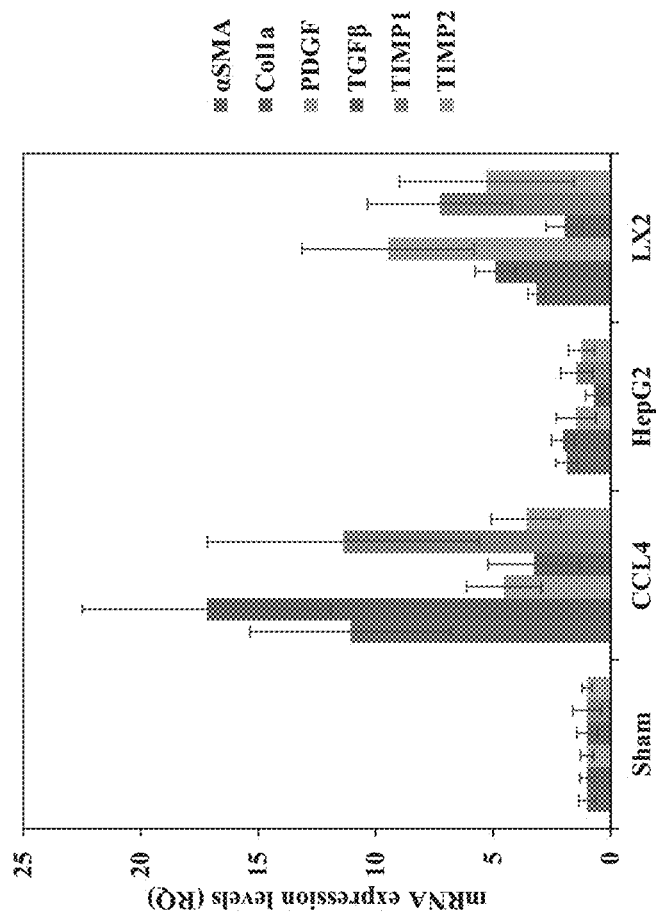
Figure 20D:
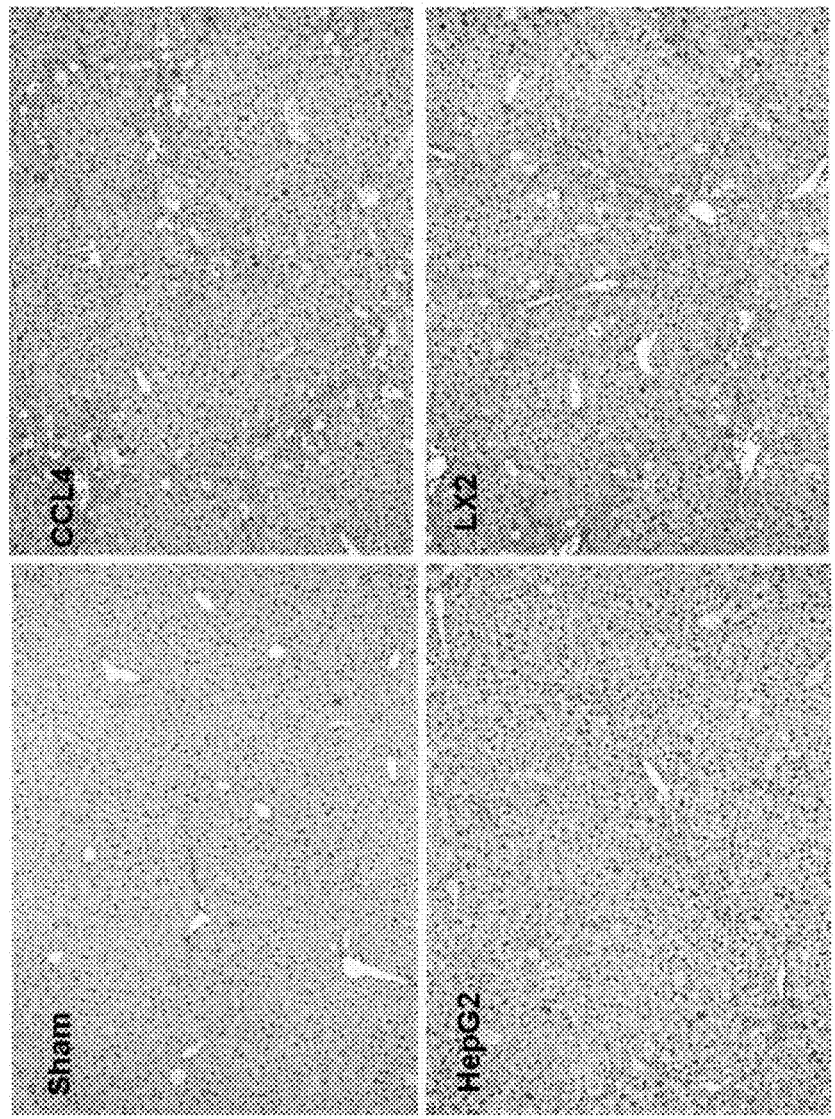
Figure 20E:
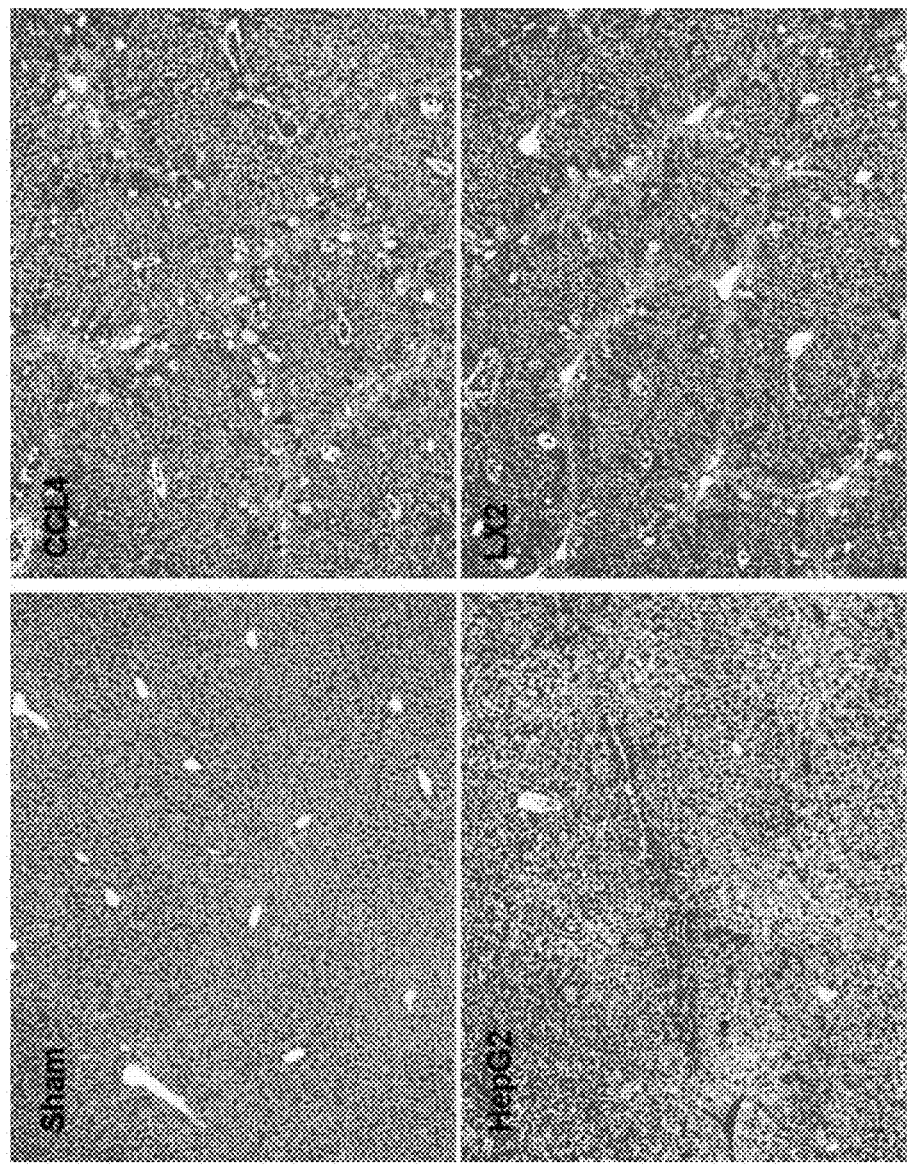

The levels of liver damage and fibrosis were evaluated by measuring liver enzymes (FIG. 20A), assessing RNA (FIG. 20B) and protein levels (FIG. 20C) of αSMA in the livers, pathologic analysis of the liver for H&E (FIG. 20D) and staining using masson trichrome (FIG. 20E). All of these analyses show that there is a marked reduction in the fibrosis levels in the livers of mice treated with the hepatocyte exosomes as compared to the CCL4 only or mice that were treated with the LX2 exosomes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a hepatic disease in a subject in need thereof comprising administering to the subject a therapeutically effective amount of miRNA-30c-2-3p or miRNA-423-5p, thereby treating the hepatic disease.

2. The method of claim 1, further comprising administering to the subject miRNA-532-5p.

3. A method of treating a disease associated with fibrosis in an organ or tissue of the subject selected from the group consisting of kidney, lung, liver, skin, bone, bone marrow, an endocrine organ and an organ of the gastrointestinal system, in need thereof comprising administering to the subject a therapeutically effective amount of miRNA-423-5p and at least one miRNA selected from the group consisting of hsa-miR-452-3p, hsa-miR-224-3p, hsa-miR-378i, hsa-miR-10b-5p, hsa-miR-99a-3p, hsa-miR-105-3p, hsa-miR-224-5p, hsa-miR-10b-3p, hsa-miR-338-5p, hsa-miR-767-5p, hsa-miR-196b-5p, hsa-miR-148a-3p, hsa-miR-452-5p, hsa-miR-873-5p, hsa-miR-873-3p, hsa-let-7a-3p, hsa-miR-208b-3p, hsa-miR-582-3p, hsa-miR-196a-5p, hsa-miR-99b-3p, hsa-miR-320d, hsa-let-7e-3p, hsa-miR-378a-3p, hsa-miR-183-5p, hsa-miR-532-5p, mir18, hsa-miR-3529-3p, hsa-miR-3074-5p, hsa-let-7f-1-3p, hsa-let-7c-3p, hsa-miR-378c, hsa-miR-486-5p, hsa-miR-185-3p, hsa-miR-320e, hsa-miR-182-5p, mir78, hsa-miR-340-3p, hsa-miR-24-2-5p, hsa-miR-330-3p, hsa-miR-192-3p, hsa-miR-26a-2-3p, hsa-miR-26b-3p, hsa-miR-99a-5p, hsa-miR-148b-3p, hsa-miR-374a-3p, hsa-miR-30a-3p, mir32, hsa-miR-17-3p, hsa-miR-193b-5p, hsa-let-7i-5p and hsa-miR-19b-3p, thereby treating the disease associated with fibrosis.

4. The method of claim 3, wherein said at least one miRNAs is selected from the group consisting of hsa-miR-452-3p, hsa-miR-224-3p, hsa-miR-378i, hsa-miR-10b-5p, hsa-miR-99a-3p, hsa-miR-224-5p, hsa-miR-10b-3p, hsa-miR-148a-3p, has-let-7a-3p, hsa-miR-196a-5p, hsa-miR-99b-3p, hsa-miR-320d, hsa-let-7e-3p, hsa-miR-378a-3p, hsa-miR-1835p, hsa-miR-532-5p, hsa-miR-3529-3p, hsa-miR-3074-5p, hsa-let-7f-1-3p, hsa-let-7c-3p and hsa-miR-486-5p.

5. The method of claim 3, wherein said at least one miRNA is selected from the group consisting of miR-196a-5p, miR378a-3p, miR-532-5p and miR-378i.

6. The method of claim 1, wherein said hepatic cells comprise primary hepatic cells.

7. The method of claim 1, wherein said hepatic cells comprise transformed hepatic cells.

8. The method of claim 1, wherein said at least one miRNA is comprised in a hepatic cell-conditioned medium.

9. The method of claim 1, wherein said at least one miRNA is an isolated miRNA.

10. The method of claim 1, wherein said hepatic disease is selected from the group consisting of hepatitis, an autoimmune hepatic disease, alcoholic steatohepatitis (ASH) and non-alcoholic steatohepatitis (NASH).

11. The method of claim 1, wherein said hepatitis disease is chronic viral hepatitis B or chronic viral hepatitis A.

* * * * *

SEQUENCE LISTING

```
<160> NUMBER OF SEQ ID NOS: 59

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
actggaagag cggagagtac                                                    20

<210> SEQ ID NO 2
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 2
gcacagacgg ctgagtag                                                      18

<210> SEQ ID NO 3
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 3
ctgccgagcg tgagattg                                                      18

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
aggcagttcg tagctcttct                                                    20

<210> SEQ ID NO 5
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 5
acccgttgaa ccccatt                                                       17
```

```
<210> SEQ ID NO 6
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 6
tccaatcggt agtagcg                                                    17

<210> SEQ ID NO 7
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 7
cucaucugca aagaaguaag ug                                              22

<210> SEQ ID NO 8
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 8
aaaauggugc ccuagugacu aca                                             23

<210> SEQ ID NO 9
<211> LENGTH: 21
<212> TYPE: RNA
<213> ORGANISM: Artificial sequence
<220> FEATURE:
<223> OTHER INFORMATION: Single strand RNA oligonucleotide

<400> SEQUENCE: 9
acuggacuag gagucagaag g                                               21

<210> SEQ ID NO 10
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 10
uacccuguag aaccgaauuu gug                                             23

<210> SEQ ID NO 11
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 11
caagcucgcu ucuauggguc ug                                              22

<210> SEQ ID NO 12
<211> LENGTH: 22
<212> TYPE: RNA
<213> ORGANISM: Artificial sequence
<220> FEATURE:
<223> OTHER INFORMATION: Single strand RNA oligonucleotide
```

<400> SEQUENCE: 12
acggauguuu gagcaugugc ua                                                22

<210> SEQ ID NO 13
<211> LENGTH: 21
<212> TYPE: RNA
<213> ORGANISM: Artificial sequence
<220> FEATURE:
<223> OTHER INFORMATION: Single strand RNA oligonucleotide

<400> SEQUENCE: 13
caagucacua gugguuccgu u                                                 21

<210> SEQ ID NO 14
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 14
acagauucga uucuagggga au                                                22

<210> SEQ ID NO 15
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 15
aacaauaucc uggugcugag ug                                                22

<210> SEQ ID NO 16
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 16
ugcaccaugg uugucugagc aug                                               23

<210> SEQ ID NO 17
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 17
uagguaguuu ccuguuguug gg                                                22

<210> SEQ ID NO 18
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 18
ucagugcacu acagaacuuu gu                                                22

<210> SEQ ID NO 19

```
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 19
aacuguuugc agaggaaacu ga                                            22

<210> SEQ ID NO 20
<211> LENGTH: 21
<212> TYPE: RNA
<213> ORGANISM: Artificial sequence
<220> FEATURE:
<223> OTHER INFORMATION: Single strand RNA oligonucleotide

<400> SEQUENCE: 20
gcaggaacuu gugagucucc u                                             21

<210> SEQ ID NO 21
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 21
ggagacugau gaguucccgg ga                                            22

<210> SEQ ID NO 22
<211> LENGTH: 21
<212> TYPE: RNA
<213> ORGANISM: Artificial sequence
<220> FEATURE:
<223> OTHER INFORMATION: Single strand RNA oligonucleotide

<400> SEQUENCE: 22
cuauacaauc uacugucuuu c                                             21

<210> SEQ ID NO 23
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 23
auaagacgaa caaaagguuu gu                                            22

<210> SEQ ID NO 24
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 24
uaacugguug aacaacugaa cc                                            22

<210> SEQ ID NO 25
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 25
```

```
uagguaguuu cauguuguug gg                                              22

<210> SEQ ID NO 26
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 26
caagcucgug ucugggguc cg                                               22

<210> SEQ ID NO 27
<211> LENGTH: 19
<212> TYPE: RNA
<213> ORGANISM: Artificial sequence
<220> FEATURE:
<223> OTHER INFORMATION: Single strand RNA oligonucleotide

<400> SEQUENCE: 27
aaaagcuggg uugagagga                                                  19

<210> SEQ ID NO 28
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 28
cuauacggcc uccuagcuuu cc                                              22

<210> SEQ ID NO 29
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 29
acuggacuug gagucagaag gc                                              22

<210> SEQ ID NO 30
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 30
uauggcacug guagaauuca cu                                              22

<210> SEQ ID NO 31
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 31
caugccuuga guguaggacc gu                                              22

<210> SEQ ID NO 32
<211> LENGTH: 22
<212> TYPE: RNA
```

```
<213> ORGANISM: Artificial sequence
<220> FEATURE:
<223> OTHER INFORMATION: Single strand RNA oligonucleotide

<400> SEQUENCE: 32
cugggagaag gcuguuuacu cu                                            22

<210> SEQ ID NO 33
<211> LENGTH: 18
<212> TYPE: RNA
<213> ORGANISM: Artificial sequence
<220> FEATURE:
<223> OTHER INFORMATION: Single strand RNA oligonucleotide

<400> SEQUENCE: 33
gccugucuga gcgucgcu                                                 18

<210> SEQ ID NO 34
<211> LENGTH: 24
<212> TYPE: RNA
<213> ORGANISM: Artificial sequence
<220> FEATURE:
<223> OTHER INFORMATION: Single strand RNA oligonucleotide

<400> SEQUENCE: 34
aacaacaaaa ucacuagucu ucca                                          24

<210> SEQ ID NO 35
<211> LENGTH: 21
<212> TYPE: RNA
<213> ORGANISM: Artificial sequence
<220> FEATURE:
<223> OTHER INFORMATION: Single strand RNA oligonucleotide

<400> SEQUENCE: 35
guuccugcug aacugagcca g                                             21

<210> SEQ ID NO 36
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 36
ugaggggcag agagcgagac uuu                                           23

<210> SEQ ID NO 37
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 37
cuauacaauc uauugccuuc cc                                            22

<210> SEQ ID NO 38
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 38
cuguacaacc uucuagcuuu cc                                            22
```

<210> SEQ ID NO 39
<211> LENGTH: 25
<212> TYPE: RNA
<213> ORGANISM: Artificial sequence
<220> FEATURE:
<223> OTHER INFORMATION: Single strand RNA oligonucleotide

<400> SEQUENCE: 39
acuggacuug gagucagaag agugg                                          25

<210> SEQ ID NO 40
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 40
uccuguacug agcugccccg ag                                             22

<210> SEQ ID NO 41
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 41
aggggcuggc uuuccucugg uc                                             22

<210> SEQ ID NO 42
<211> LENGTH: 18
<212> TYPE: RNA
<213> ORGANISM: Artificial sequence
<220> FEATURE:
<223> OTHER INFORMATION: Single strand RNA oligonucleotide

<400> SEQUENCE: 42
aaagcugggu ugagaagg                                                  18

<210> SEQ ID NO 43
<211> LENGTH: 24
<212> TYPE: RNA
<213> ORGANISM: Artificial sequence
<220> FEATURE:
<223> OTHER INFORMATION: Single strand RNA oligonucleotide

<400> SEQUENCE: 43
uuuggcaaug guagaacuca cacu                                           24

<210> SEQ ID NO 44
<211> LENGTH: 18
<212> TYPE: RNA
<213> ORGANISM: Artificial sequence
<220> FEATURE:
<223> OTHER INFORMATION: Single strand RNA oligonucleotide

<400> SEQUENCE: 44
ggagaagccg gcgggagc                                                  18

<210> SEQ ID NO 45
<211> LENGTH: 22
<212> TYPE: RNA
<213> ORGANISM: Artificial sequence
<220> FEATURE:

<223> OTHER INFORMATION: Single strand RNA oligonucleotide

<400> SEQUENCE: 45
uccgucucag uuacuuuaua gc                                              22

<210> SEQ ID NO 46
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 46
ugccuacuga gcugaaacac ag                                              22

<210> SEQ ID NO 47
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 47
gcaaagcaca cggccugcag aga                                             23

<210> SEQ ID NO 48
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 48
cugccaauuc cauaggucac ag                                              22

<210> SEQ ID NO 49
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 49
ccuauucuug auuacuuguu uc                                              22

<210> SEQ ID NO 50
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 50
ccuguucucc auuacuuggc uc                                              22

<210> SEQ ID NO 51
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 51
aacccguaga uccgaucuug ug                                              22

-continued

```
<210> SEQ ID NO 52
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 52
ucagugcauc acagaacuuu gu                                              22

<210> SEQ ID NO 53
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 53
cuuaucagau uguauuguaa uu                                              22

<210> SEQ ID NO 54
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 54
cuuucagucg gauguuugca gc                                              22

<210> SEQ ID NO 55
<211> LENGTH: 20
<212> TYPE: RNA
<213> ORGANISM: Artificial sequence
<220> FEATURE:
<223> OTHER INFORMATION: Single strand RNA oligonucleotide

<400> SEQUENCE: 55 uucguggga accuggcgcu                                                  20

<210> SEQ ID NO 56
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 56
acugcaguga aggcacuugu ag                                              22

<210> SEQ ID NO 57
<211> LENGTH: 22
<212> TYPE: RNA
<213> ORGANISM: Artificial sequence
<220> FEATURE:
<223> OTHER INFORMATION: Single strand RNA oligonucleotide

<400> SEQUENCE: 57 cggguuuug agggcgagau ga                                               22

<210> SEQ ID NO 58
<211> LENGTH: 22
<212> TYPE: RNA
<213> ORGANISM: Artificial sequence
<220> FEATURE:
<223> OTHER INFORMATION: Single strand RNA oligonucleotide
```

```
<400> SEQUENCE: 58
ugagguagua guuugugcug uu                                        22

<210> SEQ ID NO 59
<211> LENGTH: 23
<212> TYPE: RNA
<213> ORGANISM: Artificial sequence
<220> FEATURE:
<223> OTHER INFORMATION: Single strand RNA oligonucleotide

<400> SEQUENCE: 59
ugugcaaauc caugcaaaac uga                                       23
```